US012655376B2

(12) United States Patent (10) Patent No.: US 12,655,376 B2
Wrzesinski et al. (45) Date of Patent: Jun. 16, 2026

(54) CELL CULTURE CHAMBER DEVICE FOR CELL AND TISSUE GROWTH

(71) Applicant: CelVivo ApS, Blommenslyst (DK)

(72) Inventors: Krzysztof Wrzesinski, Blommenslyst (DK); Hans Henrik Jochumsen, Blommenslyst (DK); Stephen John Fey, Blommenslyst (DK)

(73) Assignee: CelVivo ApS, Blommenslyst (DK)

( * ) Notice: Subject to any disclaimer, the term of this patent is extended or adjusted under 35 U.S.C. 154(b) by 594 days.

(21) Appl. No.: 17/928,197

(22) PCT Filed: Jun. 2, 2021

(86) PCT No.: PCT/EP2021/064742
§ 371 (c)(1),
(2) Date: Nov. 28, 2022

(87) PCT Pub. No.: WO2021/245117
PCT Pub. Date: Dec. 9, 2021

(65) Prior Publication Data
US 2023/0212491 A1 Jul. 6, 2023

(30) Foreign Application Priority Data
Jun. 4, 2020 (DK) .............................. PA202070356

(51) Int. Cl.
*C12M 3/00* (2006.01)
*C12M 1/00* (2006.01)
*C12M 1/04* (2006.01)
(52) U.S. Cl.
CPC ............ *C12M 21/08* (2013.01); *C12M 23/02* (2013.01); *C12M 23/22* (2013.01); *C12M 23/24* (2013.01); *C12M 23/38* (2013.01)

(58) Field of Classification Search
CPC ...... C12M 21/08; C12M 23/02; C12M 23/22; C12M 23/24; C12M 23/38; C12M 23/08; C12M 23/20; C12M 29/04
See application file for complete search history.

(56) References Cited

U.S. PATENT DOCUMENTS 4,749,654 A 6/1988 Karrer et al.
4,945,060 A 7/1990 Turner et al.
(Continued)

FOREIGN PATENT DOCUMENTS

CN 1834718 A 9/2006
CN 200977708 Y 11/2007
(Continued)

OTHER PUBLICATIONS

Office Action issued in corresponding Japanese Application No. 2023-501411 mailed Jul. 29, 2025.
(Continued)

*Primary Examiner* — Michael L Hobbs
(74) *Attorney, Agent, or Firm* — ICE MILLER LLP; Justin D. Swindells

(57) ABSTRACT

A cell culture chamber device for growing cell cultures and tissues. The device includes: an enclosure containing a cell culture media, the enclosure being defined partly by a first end, a second end, and a connecting wall. The first end or a part or window thereof is substantially transparent, and the second end and/or the connecting wall, or a respective part or window thereof, is/are substantially transparent/translucent. The first end is configured to be optically aligned, at least for some period of time or periodically, with the second end and/or with the connecting wall so that light or another illumination or visualisation signal, transmitted through or by the second end and/or through or by the connecting wall into the enclosure is transmitted through the cell culture
(Continued)

media and out through the first end to outside the enclosure, and e.g. to outside the cell culture chamber device.

23 Claims, 10 Drawing Sheets

(56) References Cited

U.S. PATENT DOCUMENTS

| | | | | |
|---|---|---|---|---|
| 5,449,617 | A | * | 9/1995 | Falkenberg ............ C12M 27/02 |
| | | | | 435/304.2 |
| 5,518,923 | A | | 5/1996 | Berndt et al. |
| 5,614,378 | A | | 3/1997 | Yang et al. |
| 5,888,807 | A | | 3/1999 | Palsson et al. |
| 5,989,913 | A | * | 11/1999 | Anderson ............... C12M 27/10 |
| | | | | 435/293.1 |
| 6,642,019 | B1 | | 11/2003 | Anderson et al. |
| 7,927,869 | B2 | | 4/2011 | Rosero |
| 9,850,458 | B2 | | 12/2017 | Fey |
| 2003/0021457 | A1 | | 1/2003 | Kirk |
| 2003/0032457 | A1 | | 2/2003 | Leung |
| 2003/0113905 | A1 | | 6/2003 | Ho et al. |
| 2004/0039939 | A1 | | 2/2004 | Cox et al. |
| 2004/0219659 | A1 | | 11/2004 | Altman |
| 2005/0019904 | A1 | | 1/2005 | Zarur et al. |
| 2005/0089993 | A1 | * | 4/2005 | Boccazzi ................. C12M 1/12 |
| | | | | 435/297.5 |
| 2007/0042490 | A1 | | 2/2007 | Welter et al. |
| 2007/0076865 | A1 | | 4/2007 | Lauter et al. |
| 2007/0292945 | A1 | | 12/2007 | Lin et al. |
| 2008/0032380 | A1 | | 2/2008 | Kleis et al. |
| 2012/0021452 | A1 | | 1/2012 | Bishop et al. |
| 2012/0022351 | A1 | | 1/2012 | Starr |
| 2012/0079577 | A1 | | 3/2012 | Hao et al. |
| 2013/0095300 | A1 | | 4/2013 | Hatje et al. |
| 2013/0230907 | A1 | | 9/2013 | Ahluwalia |
| 2013/0267003 | A1 | | 10/2013 | Goodwin et al. |
| 2016/0152945 | A1 | | 6/2016 | Blahul |
| 2016/0201037 | A1 | | 7/2016 | Tuan |
| 2017/0009207 | A1 | | 1/2017 | Shamir |
| 2018/0112164 | A1 | | 4/2018 | Cecchi et al. |
| 2018/0129864 | A1 | | 5/2018 | Robinson et al. |
| 2019/0119623 | A1 | | 4/2019 | Tsumura et al. |
| 2019/0300840 | A1 | | 10/2019 | Masquelier et al. |
| 2019/0352594 | A1 | | 11/2019 | Matsumoto et al. |
| 2020/0148993 | A1 | | 5/2020 | Wente et al. |
| 2020/0299630 | A1 | | 9/2020 | Sasaki |
| 2022/0243162 | A1 | | 8/2022 | Wrzesinski |
| 2023/0212491 | A1 | | 7/2023 | Wrzesinski et al. |
| 2023/0250385 | A1 | | 8/2023 | Jochumsen et al. |

FOREIGN PATENT DOCUMENTS

| | | | |
|---|---|---|---|
| CN | 101336290 | A | 12/2008 |
| CN | 101528912 | A | 9/2009 |
| CN | 102112594 | A | 6/2011 |
| CN | 103261395 | A | 8/2013 |
| CN | 204211749 | U | 3/2015 |
| CN | 207505745 | U | 6/2018 |
| CN | 109880738 | A | 6/2019 |
| CN | 209383784 | U | 9/2019 |
| CN | 111065726 | A | 4/2020 |
| EP | 0419234 | A2 | 3/1991 |
| EP | 1333085 | A2 | 8/2003 |
| EP | 1696024 | A1 | 8/2006 |
| EP | 1966367 | A1 | 9/2008 |
| EP | 2093279 | A2 | 8/2009 |
| EP | 3401387 | A1 | 11/2018 |
| JP | H04264741 | A | 9/1992 |
| JP | H06181749 | A | 7/1994 |
| JP | 2006212017 | A | 8/2006 |
| JP | 2008076088 | A | 4/2008 |
| JP | 2008534012 | A | 8/2008 |
| JP | 2009502183 | A | 1/2009 |
| JP | 2009077708 | A | 4/2009 |
| JP | 2014519309 | A | 8/2014 |
| JP | 2017200468 | A | 11/2017 |
| JP | 2019041602 | A | 3/2019 |
| JP | 2019176056 | A | 10/2019 |
| KR | 2014-0078854 | A | 6/2014 |
| TW | 201831082 | A | 9/2018 |
| WO | 2004039939 | A2 | 5/2004 |
| WO | 2004050864 | A1 | 6/2004 |
| WO | 2005027446 | A1 | 3/2005 |
| WO | WO 2005/047466 | A2 | 5/2005 |
| WO | 2007076865 | A1 | 7/2007 |
| WO | 2010143651 | A1 | 12/2010 |
| WO | 2011065445 | A1 | 6/2011 |
| WO | 2011090792 | A1 | 7/2011 |
| WO | WO 2012/022351 | A1 | 2/2012 |
| WO | WO 2012/079577 | A1 | 6/2012 |
| WO | 2013095300 | A1 | 6/2013 |
| WO | 2016108049 | A1 | 7/2016 |
| WO | 2020014188 | A1 | 1/2020 |

OTHER PUBLICATIONS

Danish Patent and Trademark Office, Search Report for Application No. PA 2020 70356, dated Oct. 27, 2020 (4 pages).

Danish Patent and Trademark Office, Search Report for Application No. PA 2020 70439, dated Oct. 27, 2020 (4 pages).

Danish Patent and Trademark Office, Search Report for Application No. PA 2020 70441, dated Nov. 3, 2020 (4 pages).

Danish Patent and Trademark Office, Search Report for Application No. PA 2020 70443, dated Nov. 3, 2020 (4 bages).

Danish Patent and Trademark Office, Search Report for Application No. PA 2020 70444, dated Oct. 28, 2020 (4 pages).

Danish Patent and Trademark Office, Search Report for Application No. PA 2020 70482, dated Dec. 16, 2020 (4 pages).

Danish Patent and Trademark Office, Search Report for Application No. PA 2021 70002, dated Jun. 30, 2021 (4 pages).

European Patent Office, International Search Report for Application No. PCT/EP2021/067777, mailed Oct. 8, 2021 (4 pages).

European Patent Office, International Search Report for Application No. PCT/EP2022/050072, mailed Jun. 1, 2022 (5 bages).

International Search Report and Written Opinion of International Searching Authority for International Application No. PCT/EP2020/068632, mailed Nov. 6, 2020 (14 pages).

European Patent Office, Extended European Search Report for Application No. 17184469, dated Jan. 8, 2020 (31 pages).

International Search Report and Written Opinion of International Searching Authority for International Patent Application No. PCT/EP2021/064742, mailed Nov. 8, 2021 (21 pages).

Office Action issued in JP 2021-575961, dated Jul. 2, 2024 [4 PAGES].

Chinese Office Action issued in corresponding Application No. 202180049402.9 mailed Jun. 6, 2025.

Chinese Office Action issued in corresponding Application No. 202080045768.4 mailed Jul. 1, 2025.

Japanese Office Action issued in corresponding Application No. 2022-574555 mailed Jul. 8, 2025.

International Search Report & Written Opinion issued in PCT/EP2021/067777, mailed Oct. 8, 2021 (11 pages).

International Search Report & Written Opinion issued in PCT/EP2022/050072, mailed Jun. 1, 2022 (9 pages).

Office Action issued in corresponding China Patent Application No. 202180060615.1 mailed Nov. 28, 2025.

Yingjun, et al.; Aerospace Medicine and Medical Engineering, vol. 15, Issue 05 dated Oct. 15, 2002.

Office Action issued in corresponding Australia Application No. 2021304789 mailed on Apr. 10, 2026.

* cited by examiner

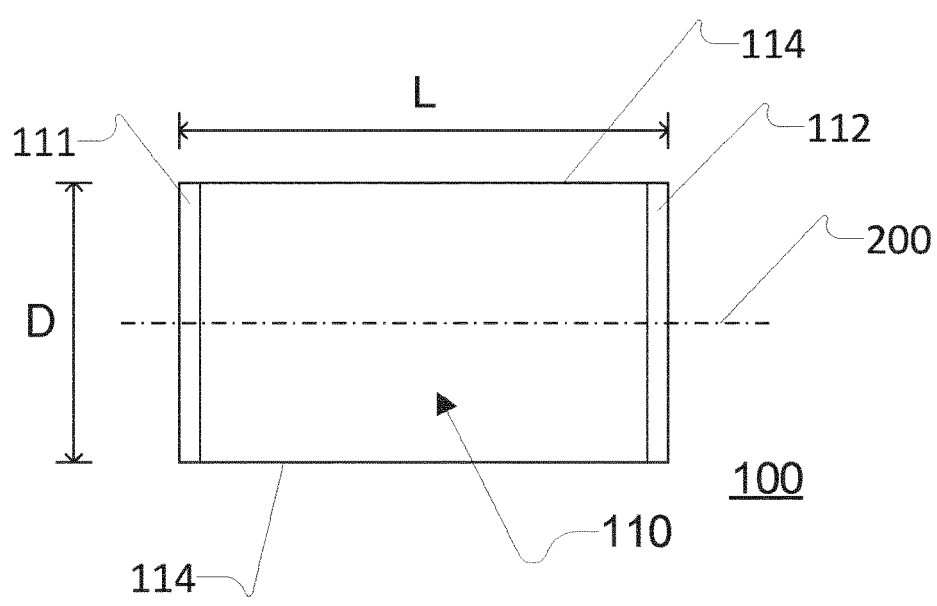
Figure 1
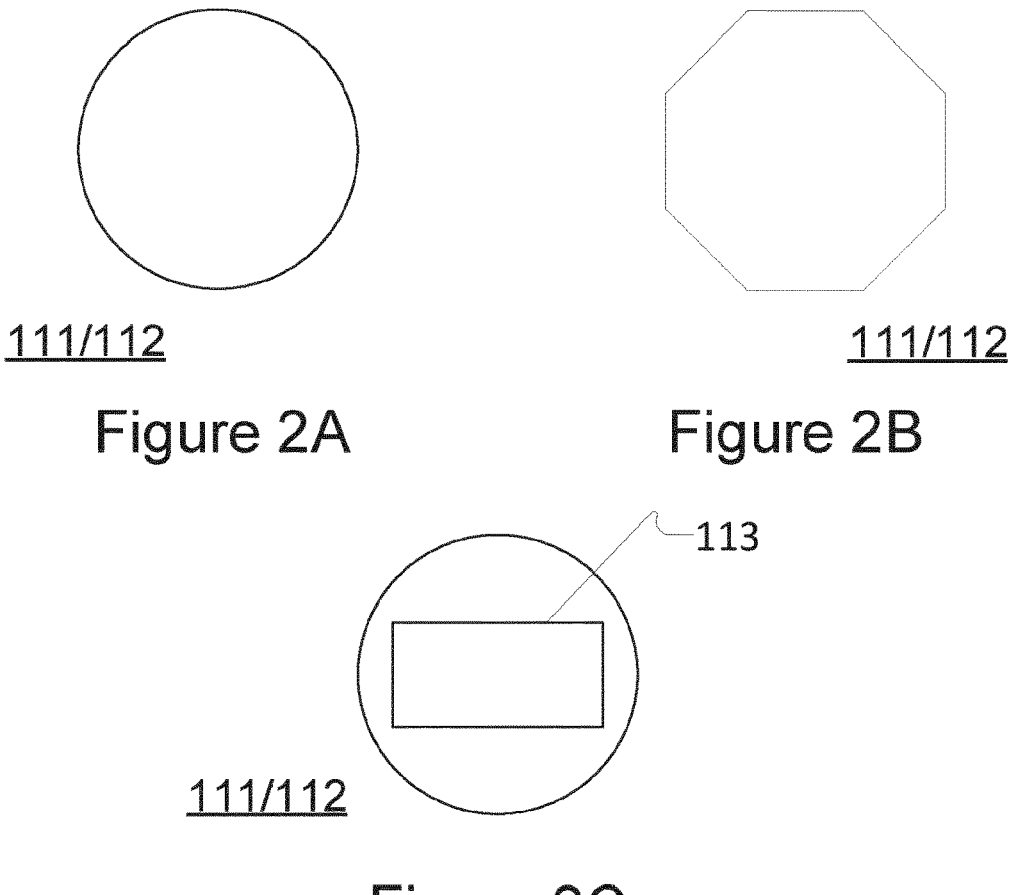
Figure 2A          Figure 2B
Figure 2C

170

145

150

104

185

140

101

112

105

100

130

190

111

120

102

103

160

101

130

150

190

111

102

103

175

CELL CULTURE CHAMBER DEVICE FOR CELL AND TISSUE GROWTH

CROSS-REFERENCE TO RELATED APPLICATIONS

This application is a U.S. National Stage of International Application No. PCT/EP2021/064742, filed Jun. 2, 2021, which claims the benefit of and priority to Denmark Patent Application No. PA202070356, filed Jun. 4, 2020, both of which are incorporated herein by reference in their respective entireties.

FIELD OF THE INVENTION

The present invention relates generally to a cell culture chamber device for the growing of cell cultures and tissues and comprising an enclosure configured to contain a cell culture media and a first end and a second end where the first and the second ends at least in part defines the enclosure. Additionally, the present invention relates to a cell culture chamber system for the growing of cell cultures and tissues comprising such a cell culture chamber device. A cell culture chamber device may also be referred to as a bioreactor.

BACKGROUND

When growing cells and tissue using more traditional cell culture chamber devices, often having an essentially flat cell support surface or the like, primary cells and biopsies tend to de-differentiate and loose their normal structural organisation and in vivo functionality. One example of this is where cells migrate from a block of tissue out onto the flat supporting surface (i.e. the so-called "melting ice-cream effect"). De-differentiated cells typically express different biochemical properties than those normally expressed by corresponding cells in an intact organism. Furthermore, certain cells have typically lost their specialised functions compared to corresponding cells in an intact organism.

Improving on this, certain cell culture chamber devices or bioreactors for the growing of cell cultures, whether a single or several cell types, or tissues, normally or even preferably use operation under omnidirectional normogravity conditions i.e. clinostat induced conditions, since this enables the preservation of the differentiated state of many types of cell in the culture. Furthermore it promotes the recovery, (or re-differentiation) of in vivo like structure and functionality in many different cell lines. This is significant because cell lines are used for the majority of cell culture work currently executed.

Such omnidirectional normogravity conditions may be induced by continuous rotation of the compartment containing the cell culture, thereby preventing the cells to adhere to the compartment walls (strictly speaking, the rotation infinitesimally increases the gravitational force (centripetal acceleration)). Suitable rotation promotes the adherence of cells to each other in a fluid environment with a minimum of shear forces acting on the culture. Shear forces can be introduced, if needed, for specific cell/tissue types, by changing the rotation speed of the bioreactor. Thereby cells aggregate into colonies typically named spheroids or organoids (in this disclosure referred to collectively as spheroids). Since pieces of tissue will be affected similarly, they are also included under the generic term spheroids.

As the spheroids grow, they get bigger and thus the rate of rotation of the bioreactor needs, for certain uses, to be adjusted to maintain optimal conditions where the spheroids remain in an essentially 'stationary orbit' relative to the bioreactor as this promotes improved uniformity of the spheroids. For other uses, the spheroids should not or need not remain in a stationary orbit but rather be allowed a different behaviour e.g. be allowed to tumble or be located on or near the bottom of the cell culture chamber, or be held against the wall of the cell culture chamber by centripetal acceleration, etc. However, in any event it is very beneficial to be able to clearly inspect the spheroids in the bioreactor at several occasions e.g. to see whether a speed adjustment should be made, and potentially to what extent. Improved uniformity of the spheroids results in a more standardised metabolic performance which then enables for example a more reliable in vitro predictive toxicological evaluation of candidate drugs prognosis of the cell culture before going into expensive clinical trials or similar, i.e. it results in a more reliable "filter" prior to embarking on animal or clinical trials.

At least for certain uses, several cell culture chamber devices or bioreactors, e.g. with different types and/or sizes/ state of cells, are used in an incubator where they all typically are located in the same—closable—open space or cavity. Even if provided with internal lighting, use in an incubator will reduce individual visibility of the content of each cell culture chamber device or bioreactor, often prompting users to repeatedly open and close—over time— the incubator and e.g. take out a cell culture chamber device or bioreactor for closer manual inspection. Repeatedly, opening and closing the incubator may at least increase the risk of contamination and temporarily disrupt the controlled environment of the incubator Patent application WO 2012/ 079577 discloses a bioreactor provided with a lid that facilitates access to an incubation cavity. Specifically the end wall of the incubation cavity is constituted by the lid so that removal of the cap renders the incubation cavity fully accessible. The disclosed bioreactor is generally cylindrical in lengthwise axis and is adapted for rotation about the lengthwise axis. The lid, the incubation cavity, an equilibrium chamber, and a reservoir chamber is 'stacked' next to each other along the lengthwise axis. The equilibrium chamber and the reservoir chamber also comprises a humidifier located centrally along the lengthwise axis. A transparent section is located in the front of the bioreactor (in the lengthwise direction) so that the cultivation of cells etc. may be monitored and assessed visually, either manually or automatically (e.g. by a camera), from outside of the bioreactor. However, even if able to monitor the content of the incubation cavity to some extent, the disclosed bioreactor does not provide optimal or enhanced viewing or registration conditions of the content of the incubation cavity, in particular due to its stacked design in the lengthwise direction obstructing at least some, and e.g. sufficient, light from reaching the incubation cavity. Additionally, the illumination often will be uneven reducing viewing or registration conditions.

Accordingly, it would be an advantage to provide a cell culture chamber device and/or a bioreactor addressing one or more of the above mentioned drawbacks, at least to an extent. In particular, it would be an advantage to provide a cell culture chamber device and/or a bioreactor enhancing viewing, both manually and automatically, of the content of the cell culture chamber, cavity, etc.

SUMMARY

It is an object to provide a cell culture chamber device and/or a bioreactor addressing one or more of the above mentioned drawbacks, at least to an extent. It is a further object to provide a cell culture chamber device and/or a bioreactor providing enhanced viewing, both manually and automatically, of the content of the cell culture chamber.

According to a first aspect, this is achieved, at least to an extent, by a cell culture chamber device for the growing of cell cultures and tissues, where the cell culture chamber device comprises an enclosure configured to contain a typically aqueous cell culture media. The cell culture chamber device further comprises a first end, a second end, and at least one connecting (e.g. circumferential) wall connecting the first and the second ends. The first end, the second end, and the at least one connecting wall at least in part defines the enclosure. The enclosure may e.g. also be referred to as a cell culture enclosure, chamber, or cavity or as an incubation cavity or chamber. The first end may e.g. also be referred to as a first end segment or first part of the enclosure and the second end may e.g. also be referred to as a second end segment or second part of the enclosure. The first end may e.g. also be referred to as a viewing end or part, or as a primary viewing end or part. The first end, or a part or window thereof, is substantially transparent. The second end and/or at least one of the at least one connecting wall, or a respective part or window thereof, is/are substantially transparent or is/are substantially translucent. The first end or the part or window thereof is configured to be optically or otherwise (e.g. or i.e. with respect to other electromagnetic radiation or mechanical waves such as sound or acoustic waves) aligned (at least for some period of time or periodically) with the second end or the part or window thereof and/or with at least one of the at least one connecting wall or the part or window thereof so that light or another illumination or visualisation signal, transmitted through or by the second end or the part or window thereof and/or through or by the at least one of the at least one connecting wall or the part of window thereof into the enclosure, is transmitted or propagates through at least a part of the cell culture media and out through the first end or the part or window thereof to outside the enclosure, and e.g. to outside the cell culture chamber device. It is noted (for relevant embodiments), that the first end (or the part or window thereof) does not need to be optically or otherwise aligned with the second end (or the part or window thereof) by being across or directly across each other, even though that provides a very expedient way of providing this. For example, a suitable optically based or other electromagnetically radiation based, sound/acoustic wave based, etc. system or one or more suitable devices or components (e.g. reflectors, mirrors, sound or light-guides, etc.) could be used to align the respective ends (or parts/windows) at least during some time. What is significant in a broadest sense is that light or another illumination or visualisation signal passes through a part or a significant part of the cell culture media in the enclosure and afterwards is emitted outside the enclosure in an as unobstructed way as possible or necessary (apart from being influenced by the content of the cell culture media) allowing registration and/or characterisation of part or all of the contents of the enclosure. In some embodiments, the first end (or at least the part or window thereof) is substantially planar as this provides an undistorted optical image or projection. However, the ends (or parts or windows) may be curved, at least to some extent. The second end and/or the connecting wall (or respective part(s) or window(s) thereof) may be curved but in some embodiments, the second end and/or the connecting wall is (or respective part(s) or window(s) thereof) is/are substantially planar.

In this way, a cell culture chamber device is provided having un-obstructed (apart from being influenced by the content of the cell culture media) light or other illumination or visualisation signal propagation paths propagating through at least a part of any cell culture media contained in the enclosure. It also enables the provision of back-light or emission of another illumination or visualisation signal from 'behind', i.e. light shone or another illumination or visualisation signal emitted through the second end and/or the connecting wall(s) (e.g. towards the second end), greatly enhancing visual inspection (manual or automatic) from the other/opposite side (i.e. via the first end). This is particularly useful e.g. for inspection of several cell culture chamber devices arranged in an incubator or the like. If the second end is transparent, then visual or other inspection (e.g. acoustic or electromagnetic radiation different from light), manual (in case of light) and/or automatic (in case of light or other electromagnetic radiation or sound or acoustic waves using a suitable sensor), is furthermore enabled from both ends, i.e. two sides, of the enclosure. In some embodiments, all the parts of the cell culture chamber device are transparent.

The light is at least in some embodiments natural or artificial light or a combination thereof, typically or preferably visible light having a wavelength of about 400 to about 700 nanometres or at least a sub-range thereof. Alternatively, the light could e.g. be infrared or near-infrared light respectively having a wavelength of about 700 nanometres to about 1 millimetre or about 900 nanometres to about 2500 nanometres. As yet another alternative, the illumination or visualisation signal is an electromagnetic radiation having a wavelength different from visible light or light, e.g. an infra-red or x-ray signal. As a further alternative, the illumination or visualisation signal is a sound or an acoustic wave signal, e.g. ultrasound. By (substantially) transparent and (substantially) translucent is meant that the ends or walls (or respective parts or windows thereof) are sufficiently (substantially) transparent and/or sufficiently (substantially) translucent in relation to the type of light or other illumination or visualisation signal intended to be used with the cell culture enclosure/the cell culture chamber device.

In some embodiments, the cell culture chamber device (and the enclosure) is configured (or at least suitable) for rotation about a (at least one) predetermined rotational axis, e.g. as generally known. In some further embodiments, the cell culture chamber device (and the enclosure) is configured for clinostat rotation or for rotation negating or supplementing, at least to a certain extent, the effects of gravitational pull on content in the cell culture chamber device or more specifically the content in the enclosure. The cell culture chamber device may e.g. comprise one or more attachment or connection elements for, preferably but not necessarily, releasably attaching or connecting with a suitable drive unit. At least some of such drive units are generally known.

In some embodiments, the cell culture chamber device is configured (or at least suitable) for a use in or as part of an incubator.

In some embodiments, the first end or the part or window thereof and the second end or the part or window thereof are opposite each other in a predetermined direction, e.g. along a central and/or length-wise axis of the enclosure and/or the cell culture chamber device where the axis extends between the first end or the part or window thereof and the second end or the part or window thereof. In some further embodiments (where the cell culture chamber device is configured for rotation as mentioned elsewhere), the central axis may also be the axis about which the cell culture chamber device is rotated or at least is rotatable.

In at least some embodiments, the enclosure is symmetrically located in the cell culture chamber device with respect to the axis of rotation/the central axis.

In some embodiments, a material or a group of materials of one or more predetermined parts, e.g. all parts, of the enclosure and/or of the cell culture chamber device is or are opaque to UVC light (i.e. light having a wavelength range of about 100 to about 280 nanometres) where the one or more predetermined parts are configured so no or substantially no UVC light can reach inside the enclosure. In this way, it is possible to expose the whole cell culture chamber device to UVC light (using the well-known disinfecting and sterilising properties of the UVC light) without detrimental effect to the content inside the enclosure of the cell culture chamber device. In some further embodiments, the UVC opaque material or group of materials is/are or comprises an UVC opaque plastic as generally known. See e.g. https://www.gsoptics.com/transmission-curves/and for examples of UVC absorbing plastics, in particular UVC opaque plastic such as polycarbonate, polystyrene, poly(methyl methacrylate) (PMMA—commonly known as acrylic or plexiglass), polyester (e.g. OKP4) or polyetherimide (e.g. Ultem) or UVC absorbing additives https://polymer-additives.special-chem.com/product-categories/additives-light-stabilizers-uv-absorbers (see https://polymer-additives.specialchem.com/product-categories/additives-light-stabilizers-uv-absorbers), including but not limited to Tinuvin®, Uvasorb®, ADK STAB or Cel-Span®.

It is noted, that even though the provision of UVC opaque material(s) function(s) particularly well according to the first aspect, it may be used independently thereof.

In some embodiments, the cell culture chamber device further comprises a circumferential gas exchanger
  - arranged circumferentially about or along at least a part of the enclosure or about a central or lengthwise axis of the cell culture chamber device (typically the central and/or lengthwise axis of the cell culture chamber device and the central or lengthwise axis of the enclosure, as disclosed herein, will coincide or at least be substantially parallel), and e.g. or preferably about the predetermined rotational axis (if the cell culture chamber devices is configured for rotation), and
  - comprising a cavity comprising (or defining) a volume connecting a gas exchange interface of the enclosure with ambient air or gas of the cell culture chamber device.

That the gas exchanger is circumferential (and other relevant elements designated herein to be circumferential, e.g. a circumferential humidifier) is to mean that the gas exchanger is arranged as radially surrounding at least a part of the enclosure. For an enclosure with a circular cross section substantially perpendicular to the central and/or lengthwise axis and a circumferential/radially surrounding gas exchanger, the cross section of both (substantially perpendicular to the central and/or lengthwise axis) would produce an inner circle (being a surrounded part of the enclosure) and an outer surrounding ring (being the gas exchanger). See e.g. FIG. 3 for an example of this according to the illustrated embodiment. In this way, the gas exchanger is arranged off centre lengthwise (but typically still about the central and/or rotational axis) and away from the central and/or lengthwise axis (typically extending between the first and the second ends and being substantially parallel to the rotational axis), i.e. the gas exchanger is not 'stacked' next to the enclosure or any other component in a lengthwise direction but rather radially surrounding or being located around an exterior of the enclosure. This enables for much more efficient back-lighting or other illumination or visualisation by another type of illumination or visualisation signal as the gas exchanger no longer obstructs light or the illumination or visualisation signal from one or more light or illumination or visualisation signal sources located at or near the second end. Additionally, the gas exchanger will at least obstruct light or illumination or visualisation signal from one or more light or illumination or visualisation signal sources located at or near the at least one connecting wall (e.g. towards the second end) to a lesser degree.

Additionally, by having a circumferential gas exchanger, the lengthwise extent of the cell culture chamber device is also greatly reduced reducing the lengthwise 'footprint'/form-factor which may be beneficial for design considerations and shortens the light-path or path of the other illumination or visualisation signal.

It is noted, that even though the provision of such a circumferential gas exchanger functions particularly well according to the first aspect (as it obstructs light or another illumination or visualisation signal at least to a lesser degree), it may be used independently thereof.

In some embodiments, the gas exchange interface is or comprises a circumferential gas permeable membrane, e.g. a semipermeable membrane, either porous or non-porous, configured to exchange gases, such as oxygen and carbon dioxide, with an inside and/or content of the enclosure, where the circumferential gas permeable membrane is arranged circumferentially along a circumferential part of the enclosure.

In some embodiments, the circumferential gas permeable membrane constitutes at least a part, e.g. or preferably all, of at least one of the at least one connecting wall of the enclosure. Accordingly, the first and the second ends together with gas permeable membrane defines the enclosure, at least in part. It is noted, that the circumferential gas permeable membrane does not need to take up a full circumference.

In some embodiments, the gas exchange interface or the circumferential gas permeable membrane is supported by at least one support structure, e.g. a grid like support structure, comprising a number of openings configured to connect the gas exchange interface or the circumferential gas permeable membrane with air or gas of the volume of the cavity of the circumferential gas exchanger.

In some embodiments, the circumferential gas exchanger is connected with the ambient air or gas of the cell culture chamber device via at least one gas or air inlet and/or outlet.

In some embodiments, at least one of the at least one gas or air inlet and/or outlet is a double vent or port configured to, e.g. or preferably simultaneously, draw in ambient air or gas into the cavity of the circumferential gas exchanger and expel air or gas out of the cavity of the circumferential gas exchanger in response to the cell culture chamber device being rotated thereby creating an air flow. The double vent or port may e.g. be configured to operate according to the Coanda effect or principle. In at least some such embodiments, mirrored but otherwise symmetric vents or ports constituting the double vent or port enables draw in and expel air or gas both in clockwise and counter clockwise rotation of the cell culture chamber device (just with reversed resulting air flow) resulting in equal rates of gas exchange when rotated in either direction (at the same speed). In some further embodiments, the degree of air movement or flow can be regulated by regulating the respective sizes of the vents of the double vent for example with a slider (e.g. regulating between 0 to about 100% of maximum air flow) or differently sized plugs (e.g. plugs for ⅓, ⅔, ⅔ of maximum air flow), or in another suitable manner.

In some embodiments, the cell culture chamber device further comprises a circumferential humidifier arranged circumferentially about at least a part of the enclosure or about a central and/or lengthwise axis of the cell culture chamber device, e.g. or preferably about the predetermined rotational axis (if the cell culture chamber device is configured for rotation), and comprises or is connected to one or more liquid or moisturising reservoirs or elements configured to humidify or moisturise air or gas in at least a part of the cavity of the circumferential gas exchanger or of the air flow.

It is noted, that even though the provision of such a circumferential humidifier functions particularly well according to the first aspect, it may be used independently thereof.

In some embodiments, the one or more liquid or moisturising reservoirs or elements is/are configured to humidify or moisturise air or gas in the vicinity of or being adjacent to at least a part of the gas exchange interface or the circumferential gas permeable membrane, the part being outside the enclosure.

In some embodiments, at least one of the one or more liquid or moisturising reservoirs or elements comprises a liquid being either a sterile aqueous solution (or at least an initially sterile aqueous solution) or an aqueous solution containing one or more additives configured to maintain sterility and/or other compounds extending shelf life and/or a predetermined function or utility, e.g. a coloured dye to aid visualisation of remaining water content of the content of the enclosure. It is noted, that the sterile aqueous solution during use typically and eventually will become non-sterile.

In some embodiments, at least one of the one or more liquid or moisturising reservoirs or elements comprises a water or solute-containing material such as a gel, sponge, or a particulate material (e.g. water- or aqua beads, slush powder or water gel powder (also referred to as "snow"), etc.). Water or aqua beads are sometimes also referred to as water crystal gel, hydrated water gel, or gel beads and is any gel that absorb and contain a relatively large amount of water. They are typically spherical and may e.g. be composed of a water-absorbing superabsorbent polymer (SAP, also known as slush powder in dry form) such as a polyacrylamide e.g. sodium polyacrylate.

It is noted, that even though the provision of such (solid) moisturising elements functions particularly well according to the first aspect, it may be used independently thereof.

In some embodiments, a material or a group of materials of the one or more liquid or moisturising reservoirs or elements and/or one or more predetermined parts of the cell culture chamber device is configured to allow transmission of UVC light to decontaminate a content of the one or more liquid or moisturising reservoirs or elements.

In some embodiments, the cell culture chamber device comprises a first or central housing (may in some embodiments also be referred to as face plate or similar) and a cover where the first or central housing comprises the second end and the cover comprises the first end, and wherein the first or central housing is configured to receive, e.g. releasably, the cover, where a cavity between the first or central housing and the cover is defined when the cover is received by the first or central housing, and where the (resulting) cavity (between the first or central housing and the cover) defines at least a part of the enclosure. In this way, the enclosure is provided (at least in part) in a particular expedient way.

In some embodiments, the cavity between the first or central housing and the cover comprises the circumferential gas permeable membrane constituting at least a part of the at least one connecting wall of the enclosure thereby connecting the first end of the cover with the second end of the first or central housing.

In some embodiments, the cell culture chamber device further comprises a main housing configured to receive the first or central housing and the cover. In some further embodiments, the main housing comprises an opening aligning with the second end of the first or central housing when the first or central housing is received by or in the main housing, where the size of the opening is substantially of the same size as the second end. Accordingly, the main housing (given the opening) will not block a line of sight to the second end. In some further embodiments, the main housing and the first or central housing comprises elements that fit tightly together obviating the need for sealing materials e.g. gluing, welding, compressible parts (e.g. o-rings), etc.

In some embodiments, the main housing and the first or central housing, when received by the main housing defines the cavity of the circumferential gas exchanger (if such is present), and the first or central housing comprises the double vent or port arranged to be substantially perpendicular to the predetermined rotational axis, e.g. on a front side or front facing side of the main housing.

In some embodiments, the first or central housing comprises the at least one (e.g. grid like) support structure comprising a number of openings.

In some embodiments, the second end or the part or window thereof is substantially transparent (instead of substantially translucent) and the cell culture chamber device further comprises or is connected to a light diffusor (also referred to as optical diffusor) configured to receive light and to provide substantially uniform light to the second end or the part or window thereof thereby providing substantially uniform illumination of the cell culture media when contained in the enclosure. The light diffusor is located in the light propagation path between the light source (natural and/or artificial) and before the enclosure/the second end or the part or window thereof. The substantially uniform illumination of the cell culture media in this way readily enables (further) enhanced visual (manual or automatic) monitoring and thereby visual assessment of the content of the enclosure.

For alternative embodiments, where the second end or the part or window thereof is substantially translucent (instead of substantially transparent), the translucent end or part or window will effectively function as a light diffuser thereby saving the need for such an additional component. For further alternative embodiments, where the second end or the part or window thereof is substantially translucent (instead of substantially transparent), a light diffuser is still present, thereby in effect providing a double-diffusor (one by the translucent end or part or window thereof and one by the light diffuser) that may produce an even further uniform light distribution (at the 'cost' of some but typically not a lot of light energy).

In yet further alternative embodiments, the diffusor is not a light diffuser but a diffusor with respect to the other type of illumination or visualisation signal, e.g. an acoustic diffusor or a diffusor for electromagnetic radiation other than light.

In some alternative embodiments, the cell culture chamber device is configured for front-lighting (or other front-application of the other type of illumination or visualisation signal) either in addition to or as an alternative to back-lighting or emission of another illumination or visualisation signal from 'behind'. In some such further alternative embodiments, the diffusor (if one is present) may be replaced by a suitable reflector, e.g. a parabolic reflector.

In some alternative embodiments, the cell culture chamber device is configured for side-lighting (or other side-application of the other type of illumination or visualisation signal) either in addition to or as an alternative to back- or front-lighting or emission of another illumination or visualisation signal from 'behind' or the 'side(s)'.

In some embodiments, a respective cross section (each being substantially perpendicular to a central axis extending between the first and the second end) of the first end and/or the second end is(are) substantially circular.

The overall shape of the cell culture chamber device is preferably such that it is sufficiently suitable for rotation about at least one axis. I.e. it should preferably avoid sharp (cross-sectional perpendicular to the axis of rotation) corners as this may introduce unwanted/irregular/too large shear forces, unwanted variations in the growth environment, or similar on growing cells or tissue during rotation, which could be detrimental to an optimal and/or uniform formation of for example spheroids.

In some further embodiments, the overall shape of the cell culture chamber device is (substantially) cylindrical with the first and second ends respectively forming the circular bases of the cylinder.

This provides a simple suitable shape readily enabling simple/simpler manufacturing of the cell culture chamber device. Furthermore such a generally cylindrical shape is also very suitable for being rotated about an axis, e.g. about its (lengthwise) central axis extending between the first end (or the part or window thereof) and the second end (or the part or window thereof).

In alternative embodiments, the overall shape of the cell culture chamber device is (substantially) spherical.

Alternatively, the cross sections of the first end and/or the second end are not circular but instead the cross sections (or one of them) may e.g. be an n'th level polygon where n is equal to or larger than three and preferably equal to or larger than at least six (i.e. an hexagon), e.g. equal to or larger than eight (i.e. an octagon) or more. Preferably, n is an even number as this promotes the symmetricity of the cell culture chamber device about a central or rotational axis (that may coincide) extending between the ends. A circular cross section is approximated to a larger and larger degree as n increases.

The cross sections of the first end and/or the second end may also be elliptical.

The cell culture chamber device may have a first extent (e.g. length) and at least a second extent (e.g. height, depth, or diameter) (see e.g. 'L' and 'D' in FIG. 1). In some embodiments, the first extent/length (L) is less than the second extent/height, depth, or diameter (D), i.e. the circumferential extent is larger than the lengthwise extent (for generally cylindrical shapes and similar). In some embodiments the ratio between the first extent/L and the second extent/D is about 1:1 to about 1:10. In some further embodiments, the ratio is about 1:2 to about 1:5 and in other further embodiments, the ratio is about 1:3 to about 1:4. These embodiments respectively provide a very (lengthwise) compact cell culture chamber. The circumferential design of the gas exchanger and/or the humidifier greatly enables a higher ratio and thereby a smaller (lengthwise) form-factor.

The cross sections (and/or the shapes) of the first end and the second end may be different from each other.

In principle, the cell culture chamber device might have any suitable regular or irregular shape (while supporting rotation as described herein) but it is preferred for manufacturing purposes if the shape is relatively simple.

In some embodiments, the enclosure and/or the cell culture chamber device further comprises one or more fiducial and/or identification markers, such as identification markings, barcodes, points of reference, etc. At least some of the fiducial and/or identification markers is/are preferably machine readable. This may e.g. be advantageously used in connection with monitoring using an imaging or vision system or device. The fiducial marker(s) enables determination of the orientation of the cell culture chamber device (and e.g. in particular of the enclosure) e.g. for use with an imaging or vision system or device. An identification marker is preferably unique to the particular cell culture chamber device that it is comprised by.

In some embodiments, the cell culture chamber device further comprises one or more aligning elements (e.g. location bar and slit or slot, etc.) for aligning different parts of the cell culture chamber (e.g. for relevant embodiments aligning the cover with the first or central housing or the main housing).

In some further embodiments, an aligning element may also function in addition as a fiducial marker.

In some embodiments, the second end and/or at least one of the at least one connecting wall comprises one or more integrated light sources.

In some embodiments, the second end and/or at least one of the at least one connecting wall is/are or comprises a fluorescent light emitting element.

In some embodiments, the cell culture chamber device comprises a closable and/or sealable first port connected to the inside of the enclosure and a closable and/or sealable second port connected to the inside of the enclosure. In some further embodiments, the first port and the second port are arranged on or to separate sides of the cell culture chamber device.

According to a further aspect is provided a cell culture chamber system for the growing of cell cultures and tissues, where the cell culture chamber system comprises a cell culture chamber device according to the first aspect and/or as disclosed herein.

In some embodiments, the cell culture chamber system comprises (or alternatively is functionally connected to) an imaging, vision, or other registration or detection system or device and at least one light source or another illumination or visualisation signal source configured to emit light or the other illumination or visualisation signal received through the second end or the part or window thereof into the enclosure, wherein the imaging, vision, or other registration or detection system or device is configured to capture at least a part of light or the other illumination or visualisation signal transmitted through the first end or the part or window thereof to outside the enclosure.

The imaging or vision system or device may e.g. comprise or be one or more cameras configured to obtaining still images and/or video of the content of the enclosure e.g. as generally known. The other registration or detection system or device may e.g. be configured for registration of sound or acoustic waves (e.g. ultrasound) or for registration of electromagnetic radiation different than light (e.g. infra-red or x-rays). Such a cell culture chamber system or bioreactor with an imaging or vision system or device works particularly well with a cell culture chamber according to the first aspect as it enables enhanced inspection of the content of the enclosure from the first side. Furthermore, it enables enhanced inspection of both the first and the second side (or at least an additional part such as the connecting wall(s)) and/or readily enables efficient front-, side-, and/or back-lighting/-illumination or visualisation.

According to a second aspect is provided a cell culture chamber device for the growing of cell cultures and tissues, the cell culture chamber device comprising an enclosure configured to contain a cell culture media,
a circumferential gas exchanger arranged circumferentially about or along at least a part (e.g. the perimeter) of the enclosure or about a central and/or lengthwise axis of the cell culture chamber device, e.g. or preferably about a predetermined rotational axis of the cell culture chamber device (if the cell culture chamber device is configured for rotation), wherein the circumferential gas exchanger comprises a cavity comprising a volume connecting a gas exchange interface of the enclosure with ambient air or gas of the cell culture chamber device.

In this way, a cell culture chamber device is provided where the gas exchanger is arranged off centre (but typically still about a central axis) and away from a generally lengthwise axis (typically extending between a first and a second end of the enclosure), i.e. the gas exchanger is not 'stacked' next the enclosure or any other component in a lengthwise direction but is rather circumferentially located. The cell culture chamber device may e.g. be configured for rotation about a predetermined rotational axis.

Aspects and embodiments of the circumferential gas exchanger of the second aspect is, at least in some embodiments, the same or corresponding (with same or corresponding advantages for the same reasons) as the circumferential gas exchanger and embodiments thereof as described herein in connection with the first aspect.

In some embodiments, the gas exchange interface is a circumferential gas permeable membrane, e.g. a semipermeable membrane (either porous or non-porous), configured to exchange gases, such as oxygen and carbon dioxide, with an inside and/or content of the enclosure where the circumferential gas permeable membrane is arranged circumferentially along a circumferential part of the enclosure.

In some further embodiments, the circumferential gas permeable membrane is a connecting wall connecting a first end (e.g. as disclosed in connection with the first aspect, but not necessarily transparent) and a second end (e.g. as disclosed in connection with the first aspect, but not necessarily transparent or translucent) wherein the first end, the second end, and the connecting wall (e.g. as disclosed in connection with the first aspect, but not necessarily transparent or translucent) at least in part defines the enclosure. The first end, the second end, and the enclosure may e.g. be provided as disclosed in connection with the first aspect.

In some embodiments, the gas exchange interface or the circumferential gas permeable membrane is supported by at least one support structure, e.g. a grid like support structure, comprising a number of openings configured to connect the gas exchange interface or the circumferential gas permeable membrane with air or gas of the volume of the cavity of the circumferential gas exchanger.

In some embodiments, the circumferential gas exchanger is connected with the ambient air or gas of the cell culture chamber device via at least one gas or air inlet and/or outlet.

In some embodiments, the cell culture chamber device is configured for rotation about a predetermined rotational axis and wherein at least one of the at least one gas or air inlet and/or outlet is a double vent or port configured to, e.g. or preferably simultaneously, draw in ambient air or gas into the cavity of the circumferential gas exchanger and expel air or gas out of the cavity of the circumferential gas exchanger in response to the cell culture chamber device being rotated about the predetermined rotational axis thereby creating an air flow.

The double vent or port may e.g. be configured to operate according to the Coanda effect or principle. In some further embodiments, the degree of air movement or flow can be regulated by regulating the respective sizes of the vents of the double vent for example with a slider (e.g. regulating between 0 to about 100% of maximum air flow) or differently sized plugs (e.g. plugs for $\frac{1}{3}$, $\frac{2}{3}$, $\frac{3}{3}$ of maximum air flow), or in another suitable manner.

In some further embodiments, the cell culture chamber device further comprises a circumferential humidifier according to the first aspect and/or as disclosed herein.

According to a third aspect is provided a cell culture chamber device for the growing of cell cultures and tissues, the cell culture chamber device comprising an enclosure configured to contain a cell culture media,
a gas exchanger (that does not need to be circumferential but may be), and
a circumferential humidifier, wherein the circumferential humidifier
is arranged circumferentially about at least a part of the enclosure or about a central and/or lengthwise axis of the cell culture chamber device, e.g. or preferably about a predetermined rotational axis of the cell culture chamber device (if the cell culture chamber device is configured for rotation), and
comprises or is connected to one or more liquid or moisturising reservoirs or elements configured to humidify or moisturise air or gas in at least a part of a cavity of the gas exchanger.

Aspects and embodiments of the circumferential humidifier of the third aspect is, at least in some embodiments, the same or corresponding (with same or corresponding advantages for the same reasons) as the circumferential humidifier and embodiments thereof as described herein in connection with the first aspect.

In some embodiments, the one or more liquid or moisturising reservoirs or elements is/are configured to humidify or moisturise air or gas in vicinity of or being adjacent to at least a part of a gas exchange interface or a gas permeable membrane, the part being outside the enclosure.

In some embodiments, at least one of the one or more liquid or moisturising reservoirs or elements comprises a liquid being either a sterile aqueous solution or an aqueous solution containing one or more additives configured to maintain sterility and/or other compounds extending shelf life and/or providing a predetermined function or utility.

In some embodiments, at least one of the one or more liquid or moisturising reservoirs or elements comprises a water or solute-containing material such as a gel, sponge, or a particulate material (e.g. water- or aqua beads).

According to a fourth aspect is provided a cell culture chamber device for the growing of cell cultures and tissues, the cell culture chamber device comprising an enclosure (110) configured to contain a cell culture media,
a gas exchanger (that does not need to be circumferential but may be), and
a humidifier (that does not need to be circumferential but may be), wherein the humidifier comprises or is connected to one or more solid moisturising elements configured to humidify or moisturise air or gas in at least a part of a cavity of the gas exchanger, wherein at least one of the one or more solid moisturising elements comprises a water or solute-containing material such as a gel, sponge, or a particulate material (e.g. water- or aqua beads, slush powder, or water gel powder).

Aspects and embodiments of the one or more (solid) moisturising elements of the fourth aspect is, at least in some embodiments, the same or corresponding (with same or corresponding advantages for the same reasons) as the moisturising elements and embodiments thereof as described herein in connection with the first aspect.

According to a fifth aspect is provided a cell culture chamber device for the growing of cell cultures and tissues, the cell culture chamber device comprising an enclosure configured to contain a cell culture media, wherein a material or a group of materials of one or more predetermined parts, e.g. all parts, of the enclosure and/or of the cell culture chamber device is or are opaque to UVC light and where the one or more predetermined parts are configured so no or substantially no UVC light can reach inside the enclosure.

Aspects and embodiments of the material or a group of materials that is or are opaque to UVC light of the fifth aspect is, at least in some embodiments, the same or corresponding (with same or corresponding advantages for the same reasons) as the material or a group of materials that is or are opaque to UVC light and embodiments thereof as described herein in connection with the first aspect.

In some embodiments, the cell culture chamber device further comprises a gas exchanger (that does not need to be circumferential but may be), and a humidifier (that does not need to be circumferential but may be) comprising or being connected to one or more liquid or moisturising reservoirs or elements configured to humidify or moisturise air or gas in at least a part of a cavity of the circumferential gas exchanger, wherein a material or a group of materials of the one or more liquid or moisturising reservoirs or elements and/or one or more predetermined parts of the cell culture chamber device allows transmission of UVC light to decontaminate a content of the one or more liquid or moisturising reservoirs or elements (while still preventing UVC light from reaching inside the enclosure).

Further details and embodiments are disclosed in the following.

Definitions

All headings and sub-headings are used herein for convenience only and should not be constructed as limiting the invention in any way.

The term "cell culture" herein refers to the maintenance in the living state of any kind of cells, cell clusters, tissue-like structures, tissue biopsies, spheriods, organoids, or similar samples obtained or initially cultured by any method known in the art.

The term "cells" herein refers to primary, immortal or stem cells (including pluripotent or induced (in any way) pluripotent) or genetically modified cells from any type of living organism, whether archaea, prokaryote or eukaryote, and also includes viruses or other entities that need living cells to replicate.

The use of any and all examples, or exemplary language provided herein, is intended merely to better illuminate the invention and does not pose a limitation on the scope of the invention unless otherwise claimed. No language in the specification should be construed as indicating any non-claimed element as essential to the practice of the invention.

This invention includes all modifications and equivalents of the subject matter recited in the claims appended hereto as permitted by applicable law.

BRIEF DESCRIPTION OF THE DRAWINGS

FIG. 1 schematically illustrates a side view of an exemplary embodiment of a cell culture chamber device as disclosed herein;

FIGS. 2A-2C respectively schematically illustrates an end view of exemplary embodiments of the cell culture chamber device of FIG. 1;

DETAILED DESCRIPTION

Figure 3:
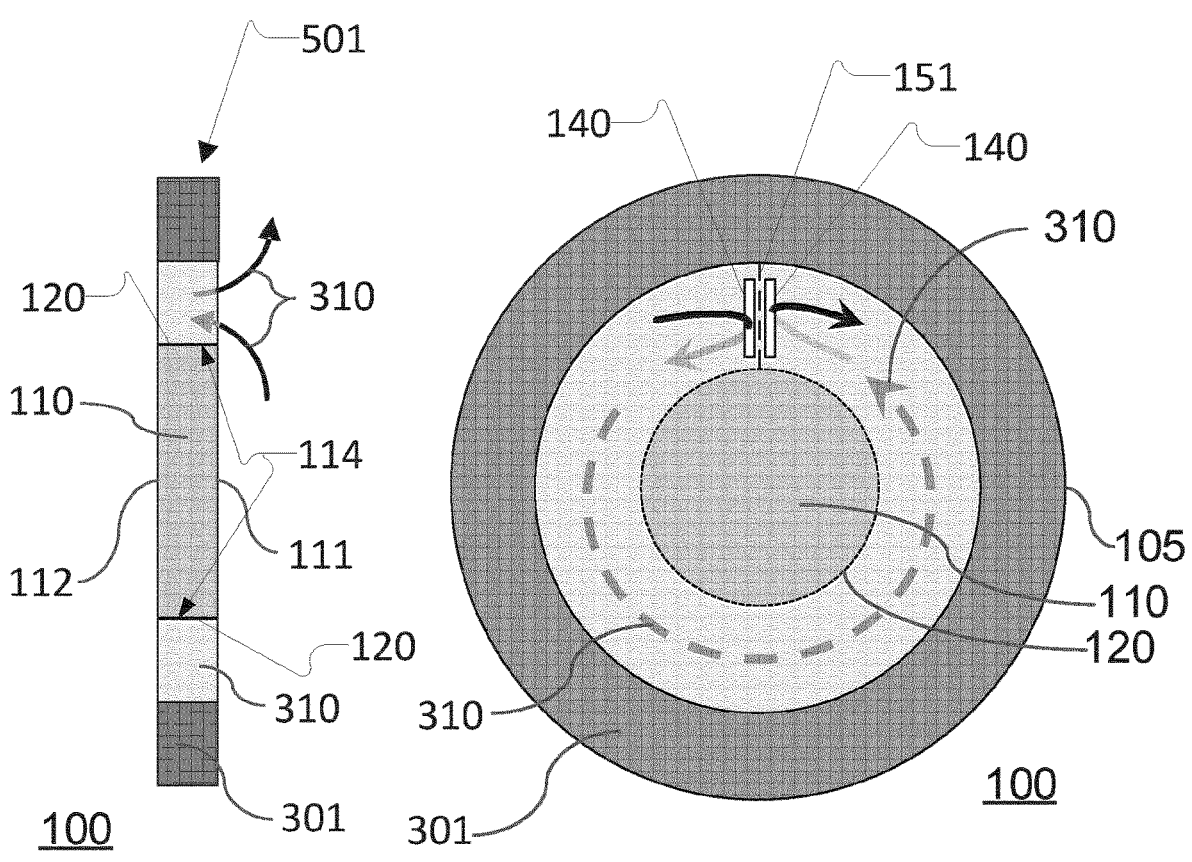
FIG. 3 schematically illustrates a front view and a cross sectional side view of embodiments of a cell culture chamber device according to some embodiments and as disclosed herein comprising a circumferential gas exchanger and a circumferential humidifier.

Various aspects and embodiments of a cell culture chamber device and a cell culture chamber system, as disclosed herein, will now be described with reference to the figures.

The shown figures are schematic representations for which reason the configuration of the different structures as well as their relative dimensions are intended to serve illustrative purposes only.

Some of the different components are only disclosed in relation to a single embodiment of the invention, but is meant to be included in the other embodiments without further explanation.

FIG. 1 schematically illustrates a side view of an exemplary embodiment of a cell culture chamber device as disclosed herein.

Illustrated is a cell culture chamber device 100 for the growing of cell cultures and tissues comprising an enclosure 110 configured to contain a cell culture media and comprising a first end 111 and a second end 112 where the first and the second ends 111, 112 at least in part defines the enclosure 110. In the shown embodiment, the first end and the second ends 111, 112 together with one or more (e.g. side or lengthwise) connecting walls, parts, segments, or the like 114 define the enclosure 110 and the cell culture chamber device 100 has—as an example—an overall substantially cylindrical shape with the first and the second ends 111, 112 respectively forming the circular bases of the cylinder (see also FIGS. 5A-5E, 6, 7A-7E, etc.). In case of an overall substantially cylindrical shape, only a single (circumferential) wall, part, segment, etc. is present connecting the first and second ends 111, 112. In some embodiments, at least one or more parts, but e.g. all, of the connecting wall, etc. 114 of the enclosure 110 is constituted by a circumferential gas permeable membrane (see e.g. 120 in FIGS. 3, 5A, 6, and 7E). It is further noted, that the enclosure 110 does not need to, and often will not, fill the entire extent of the cell culture chamber device 100 (see e.g. the following figures). In such embodiments, a housing and/or a number of housing parts (see e.g. 105, 101, and 102 in the following) may comprise the enclosure 110 (and thereby the ends 111, 112 and the one or more walls connecting the ends 111, 112).

Further illustrated is a central axis 200 extending between the first and second ends 111, 112. In at least some embodiments (and as illustrated), the cell culture chamber device 100 is configured for rotation about the central axis 200 e.g. as generally known. In at least some embodiments, the enclosure is symmetrically located in the cell culture chamber device 100 with respect to the axis of rotation/the central axis 200.

According to the first aspect, the first end 111 or a part or window (see e.g. 113 in FIGS. 2 and 5A) thereof is substantially transparent and the second end 112 or a part or window (see e.g. 113 in FIGS. 2 and 5A) thereof is substantially transparent or is substantially translucent. Furthermore, the first end 111 or the part or window thereof is configured to be optically or otherwise aligned with the second end 112 or the part or window thereof as disclosed herein. In this way, light or another illumination or visualisation signal (see e.g. 703 in FIG. 4) received through the second end 112 (or the part or window thereof) and/or through the at least one sidewall 114 (or the part or window thereof) into the enclosure 110 is transmitted through the cell culture media and out through the first end 111 or the part or window thereof to outside the enclosure 110, and e.g. outside the cell culture chamber device 100.

In some embodiments, the cell culture chamber device 100 comprises a gas exchange circuit, element, or system (not shown; see e.g. 130, 140, 151, 310, etc. in FIGS. 3, 5-9; equally referred to simply as a gas exchanger herein), e.g. as disclosed herein, configured to exchange gas (e.g. or primarily oxygen and carbon dioxide) into (e.g. oxygen) and out (e.g. carbon dioxide) of the enclosure 110. In at least some preferred embodiments, the gas exchange circuit or system is a circumferential gas exchange circuit, element, or system (see e.g. 130, 140, 151, 310, etc. in FIGS. 3, 5-9) as disclosed herein comprising a gas permeable membrane (see e.g. 120 in FIGS. 3, 5A, 6, and 7E). Alternatively, gas exchange can occur either through the sidewalls 114 of the enclosure 110, e.g. if the material of the lengthwise sidewalls 114 are polydimethylsiloxane (PDMS) (that may be produced so it is transparent) or similar, or through special filters mounted in one or more of the ends/walls 111, 112, 114. The cell culture chamber device 100 may comprise one or more special filters and/or gas inlets/outlets allowing for transfer or exchange of gas with the enclosure 110. As another alternative, the cell culture chamber device 100 is functionally connected to a gas exchange circuit or system being external to the cell culture chamber device 100.

In some embodiments, the cell culture chamber device 100 comprises a humidifier e.g. as disclosed herein. In at least some embodiments, the humidifier is configured to humidify the gas or air close to or in the vicinity of the gas exchanger and/or the gas or air that is provided to the enclosure 110. In at least some embodiments, the humidifier is preferably a circumferential humidifier (see e.g. 301 in FIG. 3) as disclosed herein. Alternatively, the cell culture chamber device 100 is functionally connected to a humidifier being external to the cell culture chamber device 100. As yet another alternative, the cell culture chamber device 100 is intended for use within an incubator or similar, providing a controlled humidified environment as generally known, in which case the cell culture chamber device 100 does not require a humidifier.

The presence of a humidifier system will eliminate or at least significantly reduce loss of liquid from the enclosure 110 and will greatly enhance the gas exchange between the enclosure 110 and the surrounding air or atmosphere for certain types of cell culture media. The difference is so significant that the cell culture chamber device 100 will normally be able to be used e.g. in an incubator without additional humidification. This typically also reduces the risk of infection in the incubator as its gaseous environment then does not need to be as humid/humidified.

Further illustrated is a first extent or length 'L' and a second extent or height or (in case of e.g. a cylindrically shaped cell culture chamber device) diameter 'D' of the cell culture chamber device (100). The extents defines, at least in part, a form-factor of the cell culture chamber device 100. In some embodiments (as illustrated), L is larger than D. However, in other embodiments (see e.g. FIGS. 5, 6, 7, etc.) L is smaller than D, i.e. the circumferential extent is larger than the lengthwise extent. In some embodiments, the ratio between L and D is about 1:1 to about 1:10, e.g. about 1:2 to about 1:5. In further embodiments, the ratio is about 1:3 to about 1:4.

The cross sections (and/or the shapes) of the first end 111 and the second end 112 may be different from each other or be the same or similar.

FIGS. 2A and 2C illustrate differently shaped cross sections of the first and/or second ends 111, 112 according to different exemplary embodiments.

The cell culture chamber device 100 may comprise one or more conduits, inlets, or access ports (not shown; see e.g. 103, 104, 140, 160, 170, etc. in subsequent Figures) e.g. gas inlet/outlet for the humidifier, liquid inlet/outlet connected to the enclosure 110 to provide access to contained cell culture media e.g. for taking out a sample of the enclosure 110 or introducing cell culture media or another liquid into the enclosure 110.

In some embodiments, (at least one of) the ends 111, 112 is a removable cover or lid providing access to the enclosure 110 when removed.

Figure 8:
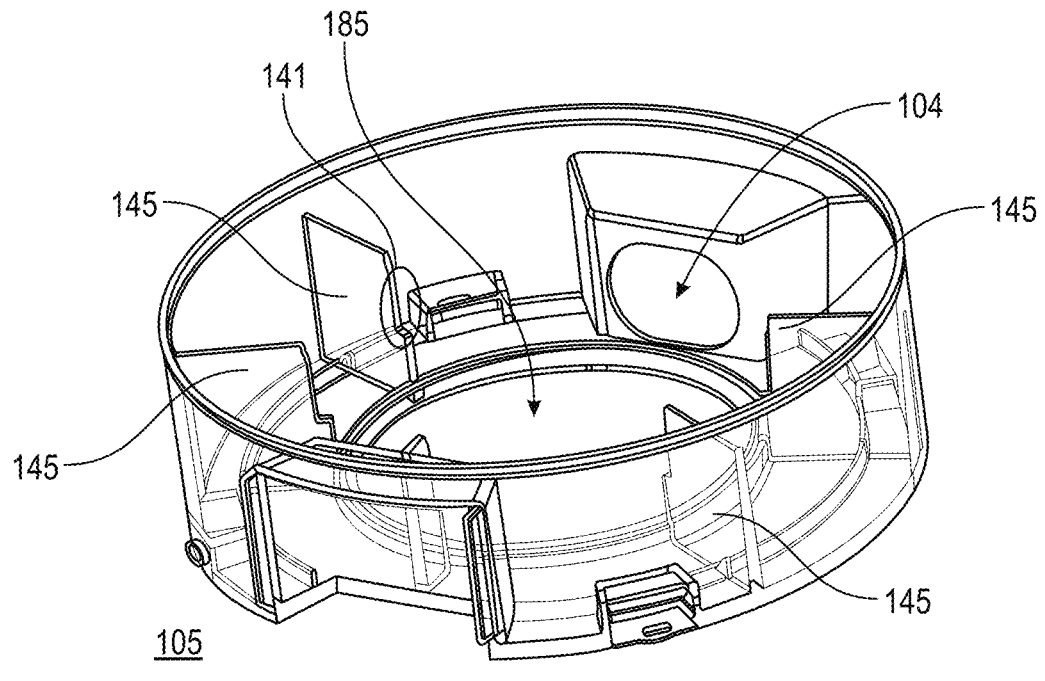
FIG. 8 schematically illustrates a perspective view of a main housing of a cell culture chamber device as disclosed herein.
Figure 9A:
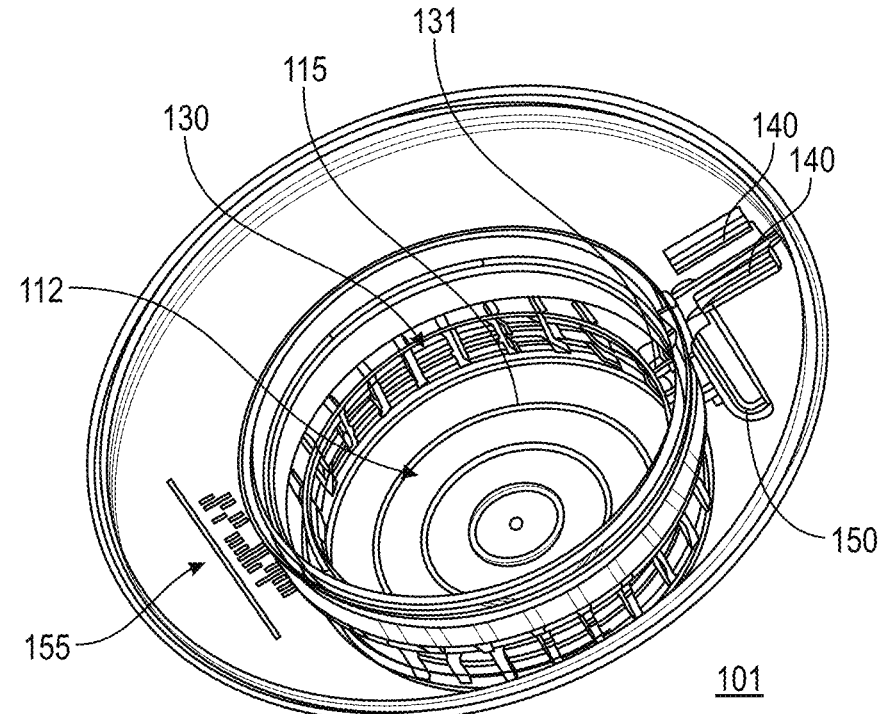
FIGS. 9A and 9B schematically illustrate two perspective views of a central housing of a cell culture chamber device as disclosed herein.
Figure 9B:
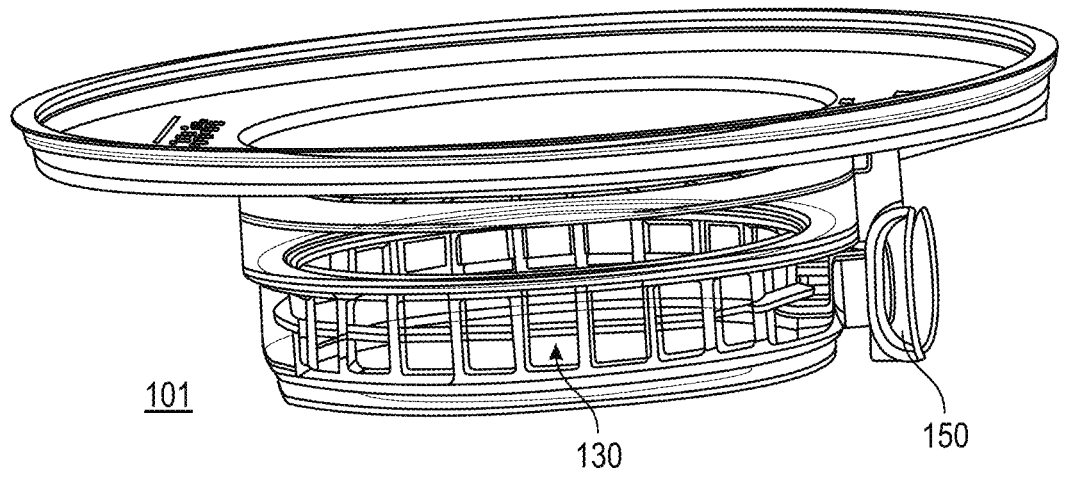
Figure 10:
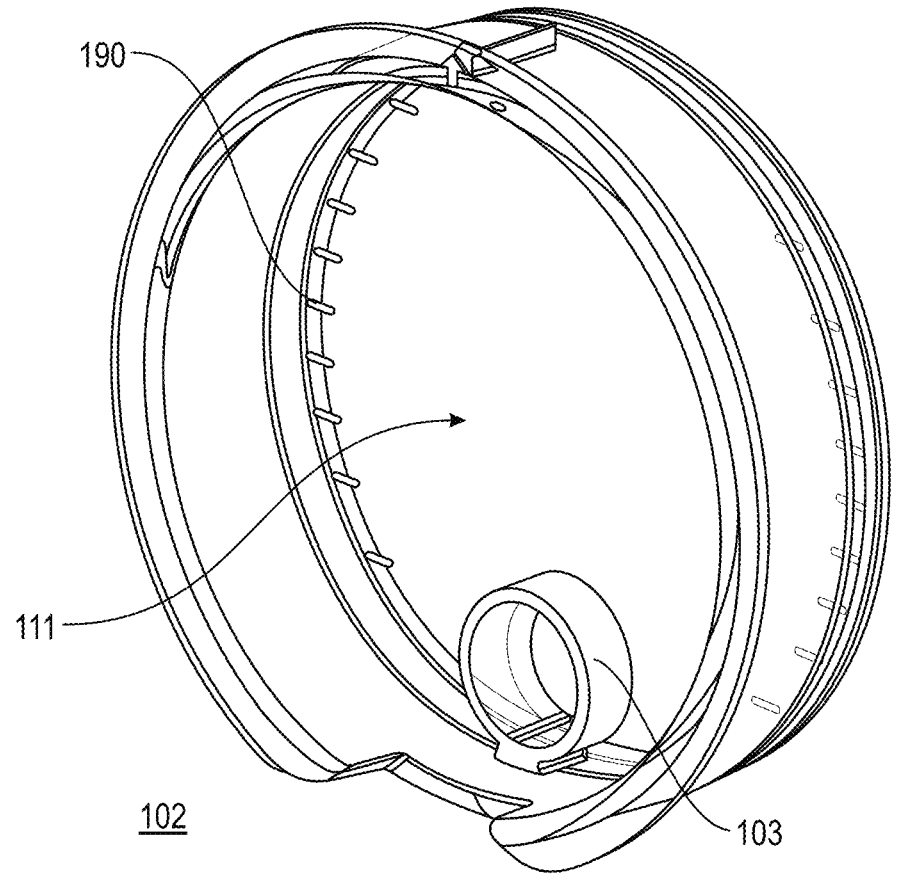
FIG. 10 schematically illustrates a perspective view of a cover of a cell culture chamber device as disclosed herein.

In some embodiments, all or substantially all the material of the cell culture chamber device 100 is transparent (rather than only one or both ends 111, 112) (see e.g. also FIGS. 8-10). In some further embodiments, all or substantially all the material of the cell culture chamber device 100 is transparent (including the first end 111) except the second end 112 that is translucent (see e.g. also FIGS. 8-11).

In some embodiments one or more ports or inlet/outlets may be used to change growth media (nutrients), add (potentially biologically active) compounds, virus, bacteria, etc. and other to the content of the enclosure 110, remove spheroids from the enclosure 110, etc.

FIGS. 2A-2C respectively schematically illustrates an end view of exemplary embodiments of the cell culture chamber device of FIG. 1.

Illustrated in FIGS. 2A and 2B is respectively an end view or a cross-sectional view of one (or both) of the ends 111, 112. As can be seen, the shape is circular (e.g. for cylindrically shaped cell culture chamber devices) in FIG. 2A and is, as an example, octagonal in FIG. 2B. As mentioned, the shape of the ends (and of the cell culture chamber device) may be any suitable shape e.g. as disclosed herein.

Shown in FIG. 2C is an end view or a cross-sectional view of one (or both) of the ends 111, 112. This corresponds to FIG. 2A except that the end(s) comprises a window 113. In such embodiments, it is the window(s) that are transparent (or translucent) rather than the entire ends 111, 112. The size and location of the window(s) 113 may be any suitable size and location but preferably should readily allow for visual or other type of inspection and control of the content of the enclosure 110.

FIG. 3 schematically illustrates a front view (shown to the right in the Figure) and a cross sectional side view (shown to the left in the Figure) of embodiments of a cell culture chamber device according to some embodiments and as disclosed herein comprising a circumferential gas exchanger and a circumferential humidifier.

Illustrated (see both views) is a cell culture chamber device 100 as disclosed herein. The cell culture chamber device 100 comprises an enclosure 100 as disclosed herein defined by a first end 111, a second end 112, and at least one connecting wall 114 connecting the ends 111, 112. The enclosure 110 is e.g. comprised by a housing/a main housing 105 where the main housing 105 is cylindrical (as an example) and centrally (as an example) comprises the enclosure 110. In the shown and corresponding embodiments, the at least one connecting wall 114 is constituted by a (supported) circumferential gas permeable membrane 120 arranged along or as a circumferential part, i.e. the perimeter or part thereof, of the enclosure 110 and being configured for exchange of gases, e.g. oxygen and carbon dioxide. The circumferential gas permeable membrane 120 may e.g. be a semipermeable membrane.

Humidification of the atmosphere close to or in the vicinity of the circumferential gas permeable membrane 120 will typically reduce or avoid cell culture media evaporation and may for certain cell culture media furthermore greatly facilitate the exchange of gases through the circumferential gas permeable membrane 120. Cells produce $CO_2$ which in solution combines with water to form bicarbonate (which is acidic). Humidification of the atmosphere results in the outer surface of the circumferential gas permeable membrane 120 becoming humid and this facilitates the escape of $CO_2$ from the culture media and in doing so slow the acidification process. This process occurs in types of cell culture that do not rely on $CO_2$ to buffer the media (e.g. those that contain HEPES, a zwitterionic sulfonic acid buffering agent). The most widely used types of growth media rely on bicarbonate in the media and $CO_2$ in the atmosphere to buffer the pH of the media. Here also humidification of the outer surface of the circumferential gas permeable membrane facilitates the 'capture' or 'release' of $CO_2$ improving stabilisation of the pH of the medium. Humidification can be provided by the cell culture chamber device 100 being located in a humidified incubator or by a humidifier as described in the following.

The cell culture chamber device 100 comprises, as shown by the front view (to the right in the Figure), a gas exchange intake and outlet for a gas exchanger that may be any suitable intake, conduit, etc. Preferably, and as shown, the gas exchange intake and outlet is in the form of a double vent or similar 140 (see e.g. also 140 e.g. in FIGS. 5A, 6, 7, and 9A) connecting the circumferential gas exchanger with outside or ambient air or gas of the cell culture chamber device 100. In the shown embodiment, the double vent 140 is, as an example, located on a front side or front facing side (see also later Figures) or similar of a housing or main housing 105. In this particular (and corresponding embodiments), the gas exchanger comprises a gas permeable membrane 120 configured to exchange gases, e.g. oxygen and carbon dioxide, with the enclosure 110/the content of the enclosure (e.g. cell culture media). In particular, oxygen may be provided into the enclosure 110 and carbon dioxide may be removed from the enclosure 110. In the shown and corresponding embodiments, the membrane 120 constitutes the (at least one) connecting wall 114 of the enclosure 110 or one or more parts thereof.

The gas exchange intake and outlet/the double vent 140 is in fluid connection with the membrane 120 thereby connecting the membrane 120 with outside or ambient air or gas of the cell culture chamber device 100. In at least some embodiments, the double vent 140 is configured to operate according to the Coanda effect or principle. In such embodiments, a wall or other suitable barrier 151 (indicated in the Figure by a straight dashed line) is located in-between the two respective vents of the double vent 140 separating and sealing them from each other at this location, i.e. in this particular example separating and sealing them in the shortest direction between them. However, the two vents of the double vent 140 are in fluid connection with each other via another path inside the housing 105 of the cell culture chamber device 100 and are also in fluid connection with at least parts of the gas exchange membrane 120 e.g. via one or more conduits, open spaces, cavities, etc. When the cell culture chamber device 100 is rotated anticlockwise, ambient air or gas is sucked into and out of the cell culture chamber device 100 via the double vent 140 as indicated by the arrows of the front view and cross-sectional side view of FIG. 3. As can be seen, air or gas is, during anticlockwise rotation, more specifically sucked into the cell culture chamber device 100 by the left (in the front view) vent 140 as indicated by the arrow going from black to grey and expelled outside the cell culture chamber device 100 by the right (in the front view) vent 140 as indicated by the arrow going from grey to black creating an internal air flow 310 with a direction as indicated by the light grey dashed circular arrow. This is the case for anticlockwise rotation. If the cell culture chamber device 100 is rotated clockwise, the direction of the airflow 310 inside the housing 105 will reverse due to symmetry, i.e. the light grey dashed circular arrow will be clockwise and air or gas is sucked in by the right vent 140 and expelled by the left vent 140.

In this way, an effective air flow 310 is readily provided being in contact with the membrane 120 and the ambient gas or air thereby e.g. expediently adding oxygen and removing carbon dioxide to/from the membrane 120 and thereby the content of the enclosure 110.

In some further embodiments, the degree of air movement or flow 310 can be regulated by regulating the respective sizes of openings of the vents of the double vent 140 for example with a slider or small or differently sized plugs or in another suitable manner.

In some further embodiments (and as shown), the cell culture chamber device 100 optionally further comprises a circumferential humidifier or humidification or moisturising element or system (herein equally referred to as humidifier) 301 configured to humidify or moisturise air or gas at least in the vicinity of the membrane 120 (at least parts thereof). A humidifier will greatly enhance a gas exchange between the content of the enclosure 110 and the ambient air or gas and will furthermore reduce or eliminate water or liquid loss from the enclosure 110 when containing a liquid or aqueous solution. The effect is so significant that the cell culture chamber device 100 will normally be able to be used in an incubator without additional humidification. This is advantageous since it typically will reduce a risk of infection in the incubator and also enables simplification of the incubator.

In some such embodiments, the circumferential humidifier 301 comprises (or is connected to) one or more liquid or moisturising reservoirs or elements. It is advantageous if the weight distribution of the circumferential humidifier 301 is at least somewhat uniformly distributed, at least to some extent, about a central axis or a rotational axis of the cell culture chamber device 100. It is also an advantage if such one or more liquid or moisturising reservoirs or elements has, or provides, a relatively large surface area for evaporation.

There are several expedient possibilities for humidifying or moisturising air or gas at least in the vicinity of the membrane 120 (at least parts thereof).

In some embodiments, the circumferential humidifier 301 comprises an element or reservoir containing (preferably sterile) liquid water or other moisturising liquid e.g. with one or more suitable filters, outlets, further (gas permeable and particularly semipermeable) membranes, etc. interfacing the water or liquid with the air flow 310 thereby humidifying or moisturising the air flow 310. The element or reservoir may e.g. be a single circumferential unit or alternatively be several separate and distinct units (e.g. evenly distributed about the central and/or rotational axis).

In alternative embodiments, the circumferential humidifier 301 comprises one or more of a water or solute-containing material such as a gel, sponge, a particulate material (e.g. water-beads, aqua-beads, etc.) that readily provides evaporation of water or liquid and efficiently influences the air flow 310. Such solid humidifying or moisturising elements may be supported or secured in the housing 105 e.g. by or to an (open) enclosure, a wall or other support structure (e.g. 145 in the following Figures).

In case of water-beads or a gel, these may be secured, adhered, pasted, etc. to an inner wall (as mentioned e.g. or preferably uniformly about the central and/or rotational axis) of the main housing/housing 105, whereby support structures are not necessary.

For embodiments not comprising a water or liquid reservoir (e.g. water-beads, gel, etc. as mentioned above) it is possible to locate such directly in a conduit, cavity, open space, etc., comprising the air flow 310, thereby greatly increasing the humidifying or moisturising effect of the air flow 310 and enabling reduction of overall space/foot-print of the cell culture chamber device 100.

It is noted, that for embodiments without a humidifier (e.g. for use in a humidified incubator or other), the shown cell culture chamber device 100 will not comprise the illustrated circumferential humidifier 301 and may have a reduced size as a result.

Figure 4:
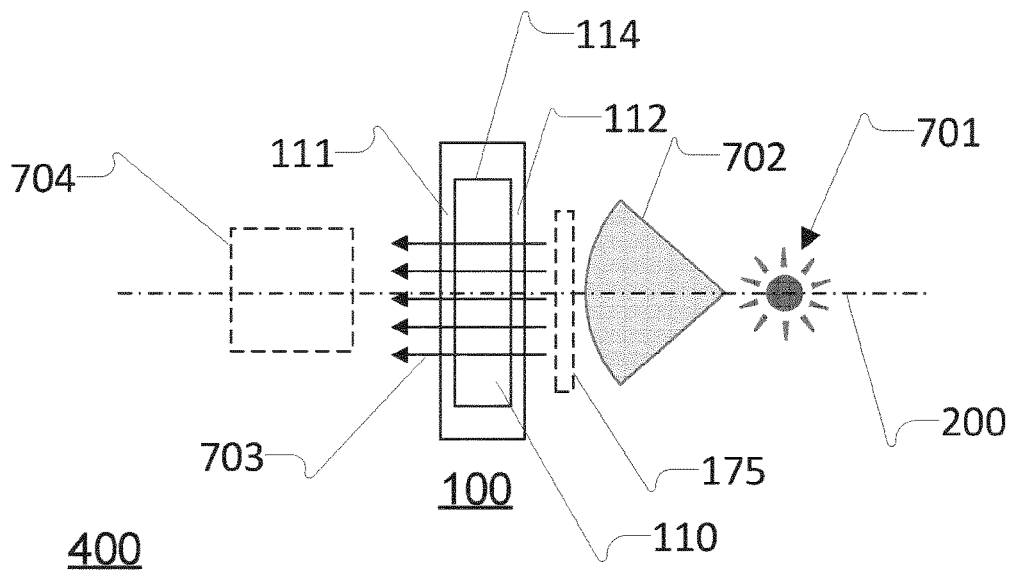
FIG. 4 schematically illustrates a cell culture chamber device as disclosed herein together with a light or another illumination or visualisation signal source and an imaging, vision, or other registration or detection unit.

FIG. 4 schematically illustrates a cell culture chamber device as disclosed herein together with a light or another illumination or visualisation signal source and an imaging, vision, or other registration or detection unit.

Illustrated is a cell culture chamber system 400 for the growing of cell cultures and tissues comprising a cell culture chamber device 100 as disclosed herein. The cell culture chamber 100 comprises a first end 111, a second end 112, at least one connecting (e.g. circumferential) wall, part, segment, or the like 114 connecting the first and the second ends 111, 112 and together defining an enclosure 110 of the cell culture chamber device 100 as disclosed herein. The cell culture chamber device 100 may e.g. be substantially cylindrical, e.g. as illustrated in FIGS. 1-3 and 5-7. Further illustrated is a central or rotational axis 200 that may coincide. The cell culture chamber device 100 may also comprise a circumferential gas exchanger comprising a circumferential gas permeable membrane (not shown; see e.g. 140, 151, 310, and 120 in FIGS. 3, 5D, 6, 7B, and 7E). The cell culture chamber device 100 may e.g. in addition also comprise a circumferential humidifier (not shown; see e.g. 301 in FIG. 3).

In at least some embodiments and as shown, the cell culture chamber system 400 comprises (or is connected to) an imaging or vision system or device 704, such as a camera or the like, and at least one light source 701 configured to emit light 702 passing into, through, and out again of the enclosure 110 (and thereby its content), where the imaging or vision system or device 704 is configured to capture at least a part of light transmitted through and out of the enclosure 110 e.g. as an image or a video. The cell culture chamber system 400 may comprise (or be connected) to a plurality of imaging or vision systems or devices and/or a plurality of light sources. The light source(s) 701 may e.g. be LED light source(s).

The light source(s) 701 emit(s), at least in some embodiments, natural or artificial light or a combination thereof, typically or preferably visible light having a wavelength of about 400 to about 700 nanometres or at least a sub-range thereof. Alternatively, the light source(s) 701 could e.g. be infrared or near-infrared light respectively having a wavelength of about 700 nanometres to about 1 millimetre or about 900 nanometres to about 2500 nanometres. The light source(s) 701 may e.g. be LED light source(s).

In some embodiments and as shown, the light source 701 is located on the side of the enclosure 100 being closest to the second end 112, e.g. on or substantially on the axis 200 where the imaging or vision system or device 704 is located generally opposite to the light source 701, i.e. on the side of the enclosure 100 being closest to the first end 111. The imaging or vision system or device 704 may be located on the axis but does not necessarily need to be, as long as the exiting light is in its field of view. In further embodiments, the first end 111 is transparent and the second end 112 is transparent or translucent. A light diffusor 175 (see e.g. 175 in FIGS. 7 and 10) may optionally be arranged in a light propagation path of light 702 from the light source 701 to or towards the enclosure 110, and in particular for the shown embodiment, be arranged before or adjacent to the second end 112. If the second end 112 is translucent and/or a light diffusor 175 is present, a more uniform lighting 703 will propagate through the enclosure and outside it to be registered or observed automatically by the imaging or vision system or device 704 and/or manually by a user.

In alternative embodiments, the connecting wall(s), etc. 114 is transparent or translucent instead of (or in addition to) the second end 112 where the light source 701 then may be arranged adjacent or at least sufficiently close to the transparent or translucent connecting wall 114 to enable sufficient light to propagate through and out of the enclosure 110. This will not be as optimal as having the light source 701 arranged opposite the first end 111 with the enclosure 110 arranged in-between (and a transparent or translucent second end 112), but may for some uses or designs be sufficient.

In some further alternative embodiments, the light source is integrated into the second end 112 (for embodiments with a transparent/translucent second end) or integrated into the connecting wall(s) 114 (for embodiments with transparent/translucent connecting wall(s) 114).

In some additionally alternative embodiments, the second end 112 or the connecting wall(s) 114 is/are or comprises a fluorescent element, e.g. a fluorescent end 112 or a fluorescent connecting wall 114.

The fluorescent element may e.g. be an IR or a NIR induced fluorescent element or any other suitable fluorescent light source or element.

The light source(s) 701 of one or more connecting wall(s) 114 may emit light directed at or towards the first end 111.

Figure 12:
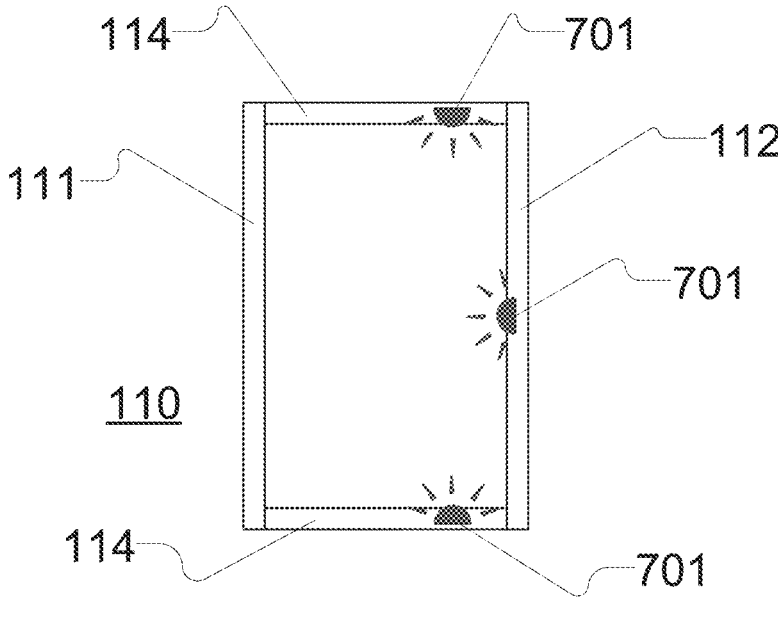
FIG. 12 schematically illustrates various embodiments with one or more light or illumination or visualisation signal sources arranged at different locations.

FIG. 12 schematically illustrates embodiments with one or more light or illumination or visualisation signal sources arranged at different locations.

As mentioned, the second end 112 and/or the connecting wall(s) 114 may comprise a transparent or transparent/translucent window (see e.g. 113 in FIG. 2 and elsewhere).

In some embodiments, the light source(s) 701 may be arranged inside the enclosure 110 e.g. adjacent to the transparent/translucent second end 112 (for relevant embodiments) or adjacent to the transparent/translucent connecting wall(s) 114 (for relevant embodiments).

In some alternative embodiments, at least some of the illustrated light source(s) 701 is/are replaced by one or more other illumination or visualisation signal sources 701, e.g. one or more acoustic transducers configured to emit acoustic waves, e.g. ultrasound, or one or more emitters configured to emit electromagnetic radiation other than light, e.g. infrared or x-rays. Furthermore, the imaging or vision system or device 704 is replaced by another registration or detection system or device configured to register the other illumination or visualisation signal. The other registration or detection system or device 704 may e.g. be configured for registration of sound or acoustic waves (e.g. ultrasound) or for registration of electromagnetic radiation different than light (e.g. infrared, x-rays).

FIGS. 5A-5E respectively schematically illustrates a front, a first ('right') side view, a first cross sectional view (AA), a second cross sectional view (CC), and a third cross sectional view (BB) of one exemplary embodiment of a cell culture chamber device as disclosed herein.

Figure 5A:
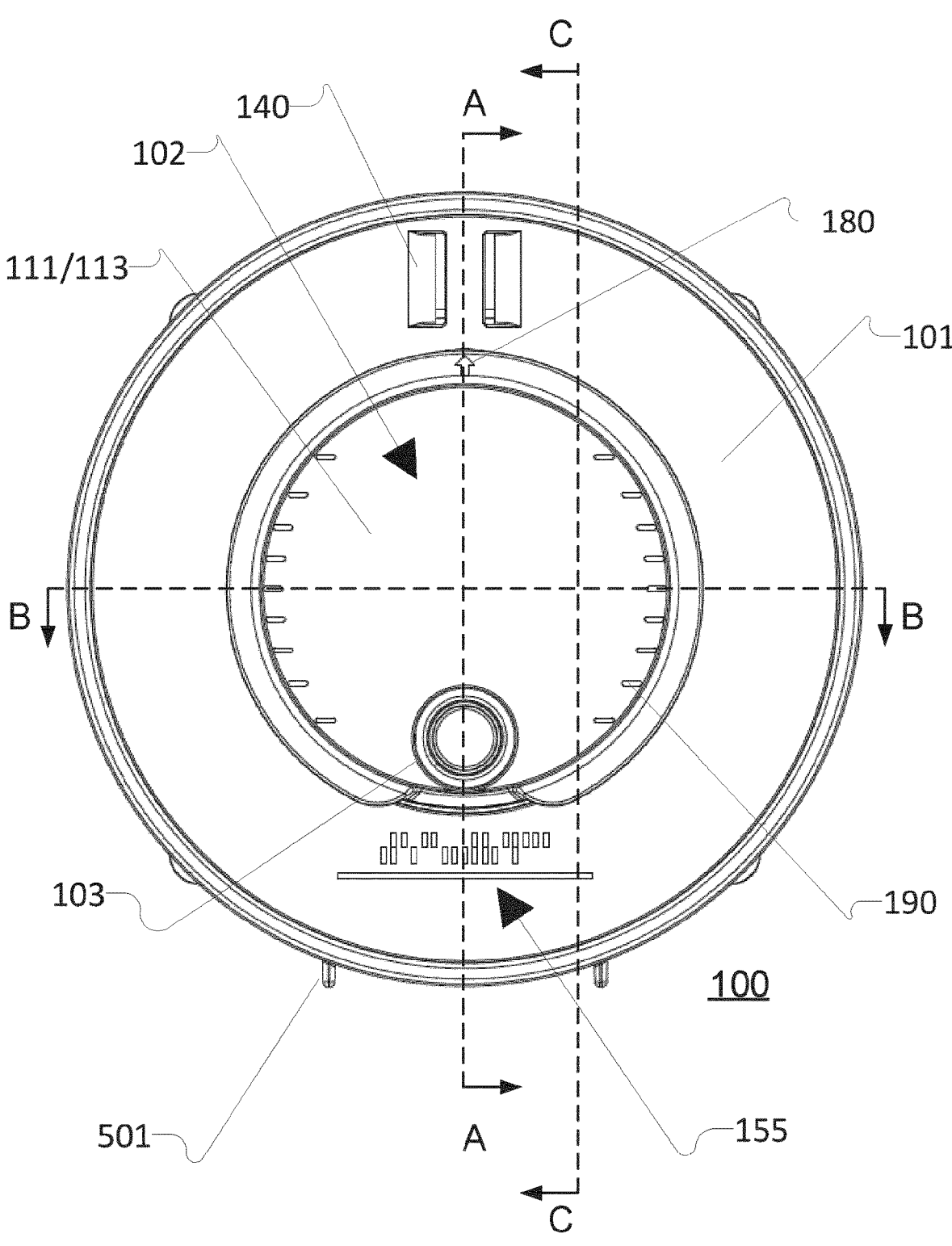
FIGS. 5A-5E respectively schematically illustrates a front, a first ('right') side view, a first cross sectional view (AA), a second cross sectional view (CC), and a third cross sectional view (BB) of one exemplary embodiment of a cell culture chamber device as disclosed herein.

Illustrated in FIG. 5A is a front view of an exemplary preferred embodiment of a cell culture chamber device as disclosed herein. Illustrated is a front of a cell culture chamber device 100 comprising a transparent first end 111. In this particular (and corresponding embodiments) a floor, bottom, or wall of a cover 102 (see e.g. also 102 in FIG. 10) constitutes a first end 111 (or a part or window 113 thereof) of the cell culture chamber device 100. The floor or bottom of the cover 102 form an enclosure (see e.g. 110 in FIGS. 5C-5E, 6, etc.) as disclosed herein together with a first or central housing 101 as will be more apparent from some of the following figures. In some embodiments (and as shown in FIGS. 5C, 5D, 5E, 6, etc.), the first or central housing 101 comprises a central cavity for (e.g. or preferably releasable) receipt of at least a part of the cover 102 and more particularly (in the shown and corresponding embodiments) for receipt of the floor or bottom of a cover 102. The first or central housing 101 and the cover 102 may e.g. comprise respective releasable securing elements (such as snap fit, bayonet, friction fit, etc. elements) to releasably secure them together. Alternatively, they may be fixed non-releasably to one another or e.g. be integrally formed.

The cell culture chamber device 100 of FIGS. 5A-5E is, as an example, shaped substantially cylindrically with a circular first end.

In this particular (and corresponding embodiments), the central housing 101 additionally comprises a gas exchange circuit, element, or system in the form of a circumferential gas exchange system comprising a circumferential gas permeable membrane (not shown; see e.g. 301 and 120 in FIGS. 3, 5D, 6, 7B, and 7E). As mentioned, the floor or bottom of the cover 102 constitutes a first end 111 (or a part or window 113 thereof) of the cell culture chamber device 100.

In this particular (and corresponding embodiments), the central housing 101 furthermore comprises a circumferential humidifier (not shown) as disclosed herein and e.g. as explained in connection with FIG. 3). Some alternative embodiments of the cell culture chamber device 100 do not comprise any humidifier, e.g. for use in a humidified incubator or other.

The central housing 101 optionally comprises a gas exchange intake and outlet for a gas exchanger as disclosed herein (see e.g. 130, 140, 151, 310, etc. in FIGS. 3, 5-9) in the form of a double vent 140 located on the front of the central housing 101.

The double vent 140 has been described in more detail e.g. in connection with FIG. 3.

Figures 5B, 5C, 5D, 5E:
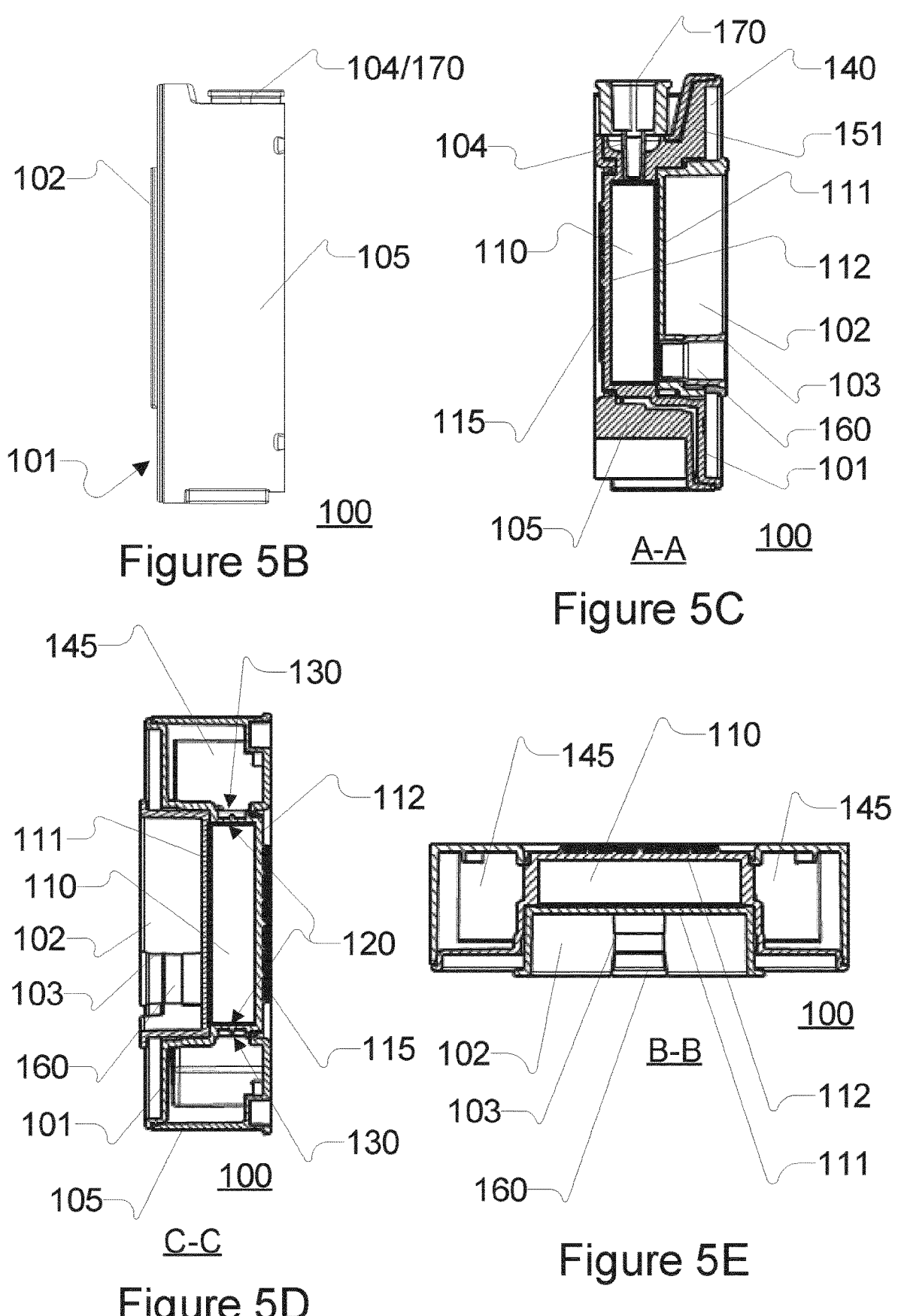

Further indicated are three cross-sections designated AA (shown in FIG. 5C), BB (shown in FIG. 5E), and CC (shown in FIG. 5D).

In some embodiments (and as shown), the cell culture chamber device 100 further comprises a closable and/or sealable (first) port 103 providing access for a user to the inside of the enclosure e.g. for taking out a sample from the enclosure (e.g. removing spheroids), emptying or filling the enclosure, etc. In the shown embodiment, the closable and/or sealable port 103 comprises a conduit (from the inside of the enclosure to outside the cell culture chamber device 100) and e.g. a simple plug or similar 160. The port 103 may advantageously be located on the top of the cell culture chamber device 100 as this may avoid or reduce bubble formation, e.g. by allowing for overflow.

In some embodiments (and as shown), the cell culture chamber device 100 further comprises one or more fiducial and/or identification markers, here an identification code 155 and a fiducial marker 180. The identification code 155 is preferably unique to the particular cell culture chamber device 100. The fiducial marker 180 enables determination of the orientation of the cell culture chamber device 100. The fiducial and/or identification markers 155, 180 is/are preferably machine readable, e.g. by a suitable imaging or vision unit or system. In some embodiments, the cell culture chamber device further comprises one or more aligning elements (e.g. location bar and slit or slot, etc.) for aligning different parts (ensuring or facilitating that a part may only be received with a proper orientation by another part) of the cell culture chamber (e.g. appropriately aligning the cover 102 with the first or central housing 101). The fiducial marker 180 may e.g. be such an aligning element (see e.g. also 131 in FIG. 9A).

Accordingly, a very compact (lengthwise) cell culture chamber device 100 is provided, in particular because of the circumferential gas exchange system and (if present) the circumferential humidifier.

Optionally, the transparent cover 102 comprises a number of level or fill-rate indicators 190 readily indicating an actual volume of cell culture media contained in the enclosure.

In some embodiments and as shown, the cell culture chamber device 100 further comprises one or more (here two) feet, standing elements or the like 501 enabling the cell culture chamber device 100 to stand and prevent it from rolling. This may make use of ports, inlets, etc. easier or more reliable (see e.g. port 170 in the following).

Illustrated in FIG. 5B is a side view of the cell culture chamber device 100 of FIG. 5A seen from the side and from right to left (according to the orientation of FIG. 5A). The shown cell culture chamber device 100 comprises a main housing 105 receiving (e.g. permanently or in a fixed way) the central housing 101 in turn receiving (e.g. releasably) the cover 102. Further shown is a (second) port 104 (or rather a plug or valve thereof 170) that is in fluid connection with and provides (additional) access to the enclosure.

The ratio between a first extent/length (in the left right direction of FIG. 5B) and the second extent/height or diameter (in the up down direction of FIG. 5B) is about 1 to about 3-4 e.g. about 1 to about 3.5 but may be different, e.g. as disclosed herein, for other embodiments.

Illustrated in FIG. 5C is a first cross sectional view as given by A-A of FIG. 5A. Illustrated is the enclosure 110 defined by the transparent first end 111 (being the floor or bottom of the cover 102, the transparent or translucent second 112 being a floor or bottom of the central housing 101, and sidewalls of the cavity of the central housing 101. Further illustrated is the main housing 105 receiving the central housing 101 and the cover 102 in a very compact way.

As mentioned, the second port 104 provides access (in addition to the first port 103) to the enclosure. As explained in connection with e.g. FIG. 3, the double vent 140 connects the outside or ambient air or gas of the cell culture chamber device 100 with the circumferential gas exchange system (see e.g. 130, 140, 151, 310, etc. in FIGS. 3, 5-9).

As can be seen, the closable and/or sealable first port 103 and its conduit connects the inside of the enclosure 110 to outside the cell culture chamber device 100. The port walls are a part of the cover 102, allowing for easy access to the content of the enclosure 110. In a similar manner, access to the inside of the enclosure 110 is afforded via the second port 104 (with plug 170). The plug walls of 104/170 are a part of the central housing 101. It is noted, that the first port 103 and the second part 104 are arranged at different sides of the cell culture chamber device 100 enabling easy access to the enclosure from several different sides of the cell culture chamber device 100.

Further illustrated is the gas exchange intake and outlet in the form of a double vent 140 as already explained.

The view of FIG. 5C is a central vertical cut viewed from left to right (in the orientation according to FIG. 5A).

Illustrated in FIG. 5D is a second cross sectional view as given by C-C of FIG. 5A and viewed from right to left.

Again, the enclosure 110, the first transparent end 111, the transparent or translucent second 112, the central housing 101, the cover 102, the closable and/or sealable ports 103 and 104, and the main housing 105 are illustrated.

Further shown, is the gas permeable membrane 120 of the circumferential gas exchange system and a (part of a) grid like structure 130 of the circumferential humidifier (see e.g. 130 in FIGS. 9A and 9B).

Also illustrated is an optional wall structure element or similar 145 for holding and/or supporting a water, liquid, or moisturizing element (explained further in connection with FIG. 8) according to some embodiments of a circumferential humidifier.

In some embodiments, the cell culture chamber device 100 optionally further comprises one or more markings 115 (see also 115 in FIG. 9A)—herein as an example in the form of a number of concentric circles 115 that may give a user some fixed marks against which to see the gentle movement of the contained spheroids. The markings 115 are (as an example) arranged on the 'outside' of the second end 112.

The view of FIG. 5D is a vertical cut shifted off-centre to the left and viewed from right to left (in the orientation according to FIG. 5A).

Illustrated in FIG. 5E is a third cross sectional view as given by B-B of FIG. 5A.

Illustrated is the enclosure 110, the first transparent end 111, the transparent or translucent second 112, the cover 102, the closable and/or sealable port 103, and two optional wall structure elements or similar 145 for holding and/or supporting a water, liquid, or moisturizing element according to some embodiments.

The view of FIG. 5E is a horizontal central cut viewed from top to bottom (in the orientation according to FIG. 5A).

It is noted, that the cell culture chamber device 100 readily enables inspection, automatic and/or manual, of the content of the enclosure 110 from two sides (as given by the first and the second ends 111, 112) if both ends 111, 112 are transparent.

In the embodiment illustrated in FIGS. 5A-5E (and corresponding ones), the second end 112 is preferably translucent rather than transparent as this provides better (more uniform) lighting of the content of the enclosure 110 while avoiding a need for a light diffusor.

Figure 6:
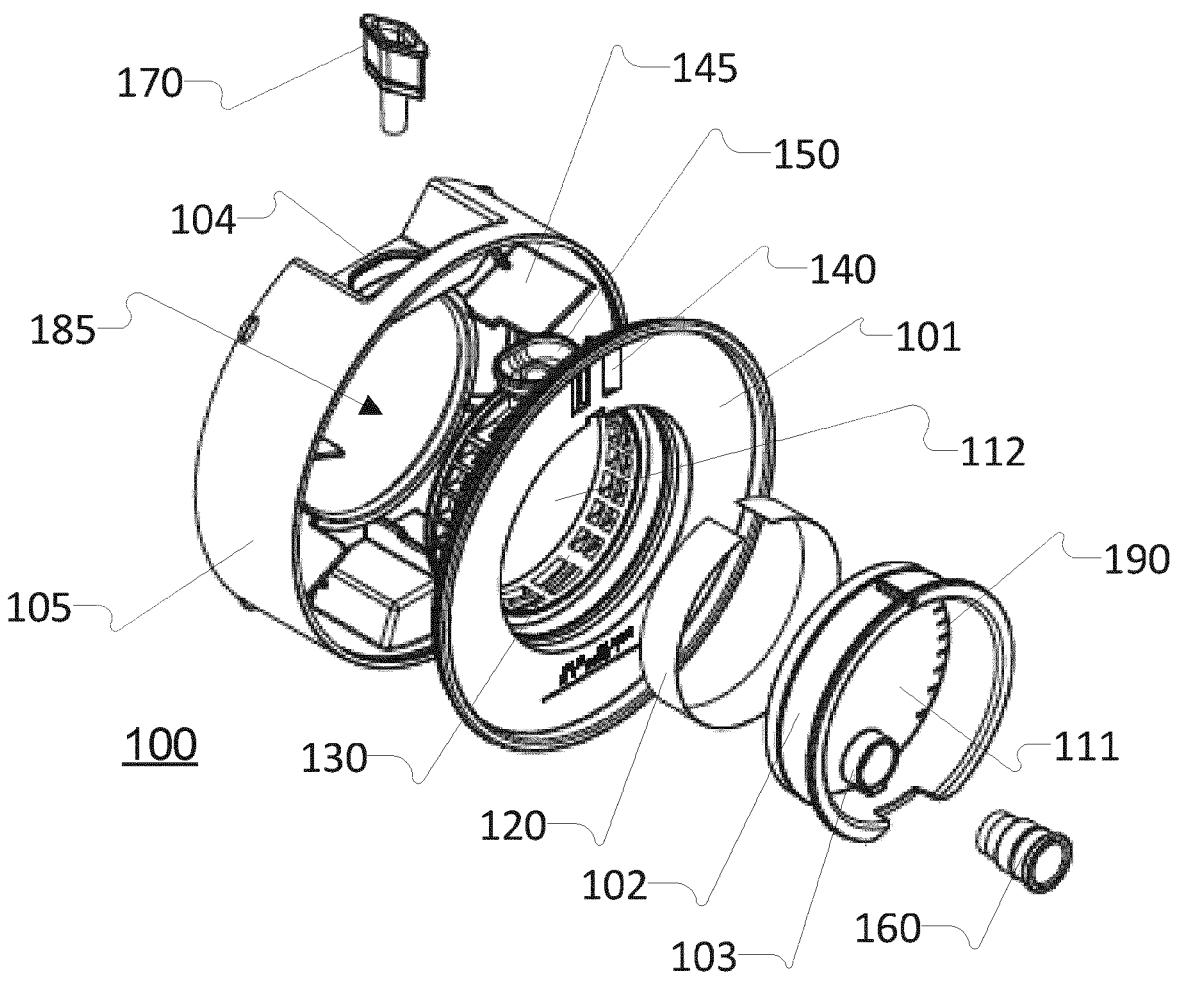
FIG. 6 schematically illustrates a perspective exploded view of the exemplary embodiment of a cell culture chamber device of FIGS. 5A-5E.

FIG. 6 schematically illustrates a perspective exploded view of the exemplary embodiment of a cell culture chamber device of FIGS. 5A-5E.

Illustrated are the elements of FIGS. 5A-5E shown in an exploded view.

FIG. 6 more clearly show the grid like structure 130 of the circumferential humidifier and the gas permeable membrane 120. In an assembled state of the cell culture chamber device 100, the gas permeable membrane 120 is located adjacent to an inside of the grid like structure 130 and the first end 111 is opposite (and optically aligned with) the second 112 and the second end 112 is aligned with an opening 185 of the main housing 105 readily enabling inspection of the content of the enclosure from that side also if the second end 112 is transparent. Further shown is a further port 150 that aligns with the first port 104 in the assembled state.

If the second end 112 is transparent, it is possible to provide lighting ('back'-lighting) from this side through the opening 185 of the main housing 105 thereby enhancing inspection (manual or automatic) from the other/opposite side (via the first end 111).

If the second end 112 is translucent, suitable (back-) lighting may provide a more uniform illumination of the content of the enclosure further enhancing inspection (manual or automatic) from the other/opposite side (via the first end 111).

If the second end 112 is transparent (or translucent), uniform lighting (or even further uniform lighting) might be provided using a light diffusor placed between the light source(s) and the second end 112, preferably close to or adjacent to the second end 112. Such an embodiment, is e.g. shown in FIGS. 7A-7E.

In some embodiments, the material of the main housing 105, the central housing 101 (and thereby the second end 112), the cover 102 (and thereby the first end 111) may e.g. be the same (transparent) material (see e.g. also FIGS. 8-10).

The embodiments of a cell culture chamber device 100 as illustrated in FIGS. 5-6 and 7 provides a very compact (in particular in a lengthwise direction) self-contained and fully functioning cell culture chamber device 100 or bioreactor where the gas exchanger (and if included, the humidifier) is arranged away from a central axis and/or an axis of rotation. In addition, the cell culture chamber device 100 has a petri-dish like design enabling easy and familiar handling.

FIGS. 7A-7E respectively schematically illustrates a first ('right') side view, a first cross sectional view (AA), a second cross sectional view (CC), a third cross sectional view (BB), and a perspective exploded view of an alternative exemplary embodiment of a cell culture chamber device as disclosed herein.

The embodiment of a cell culture chamber device 100 of FIGS. 7A-7E corresponds to the embodiment of FIGS. 5A-5E and 6 except that the second end 112 is transparent rather than translucent and that the cell culture chamber device 100 comprises a light diffusor 175 located adjacent the second end 112 (on a side facing away from the first end 111) or at least between the light source(s) and the second end 112.

In alternative embodiments, the light diffusor 175 could be contained inside the enclosure near the second end 112.

Figures 7A, 7B, 7C:
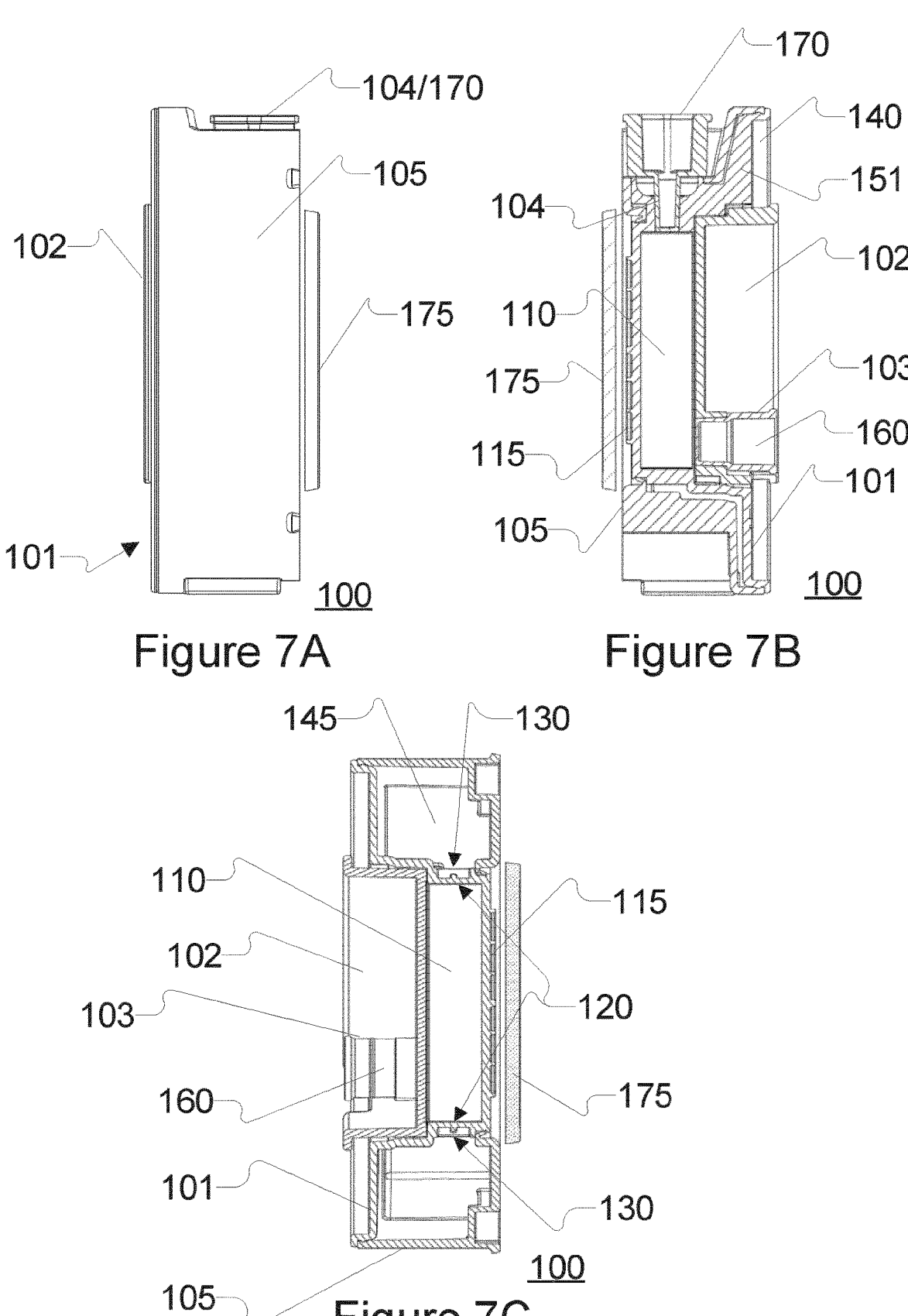
FIGS. 7A-7E respectively schematically illustrates a first ('right') side view, a first cross sectional view (AA), a second cross sectional view (CC), a third cross sectional view (BB), and a perspective exploded view of an alternative exemplary embodiment of a cell culture chamber device as disclosed herein.
Figure 7D:
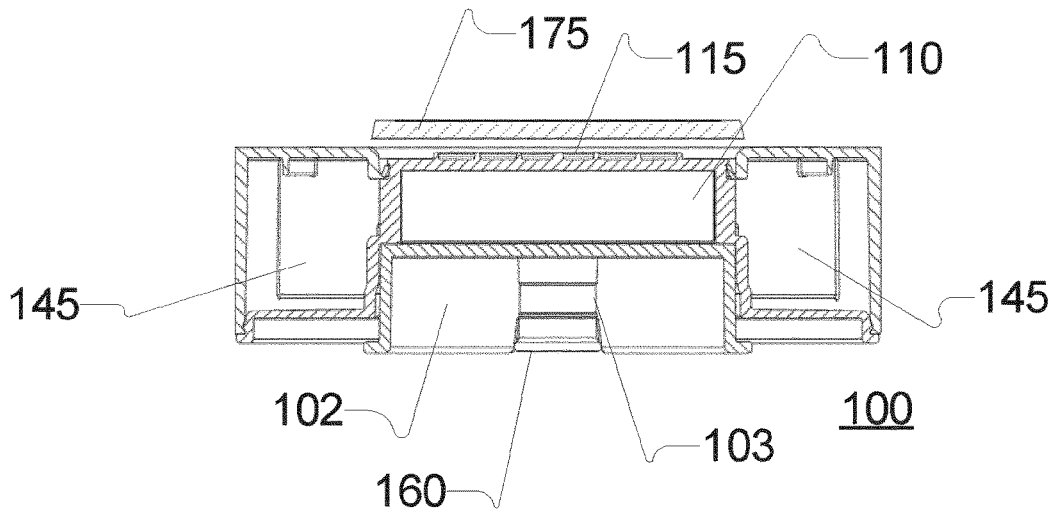
Figure 7E:
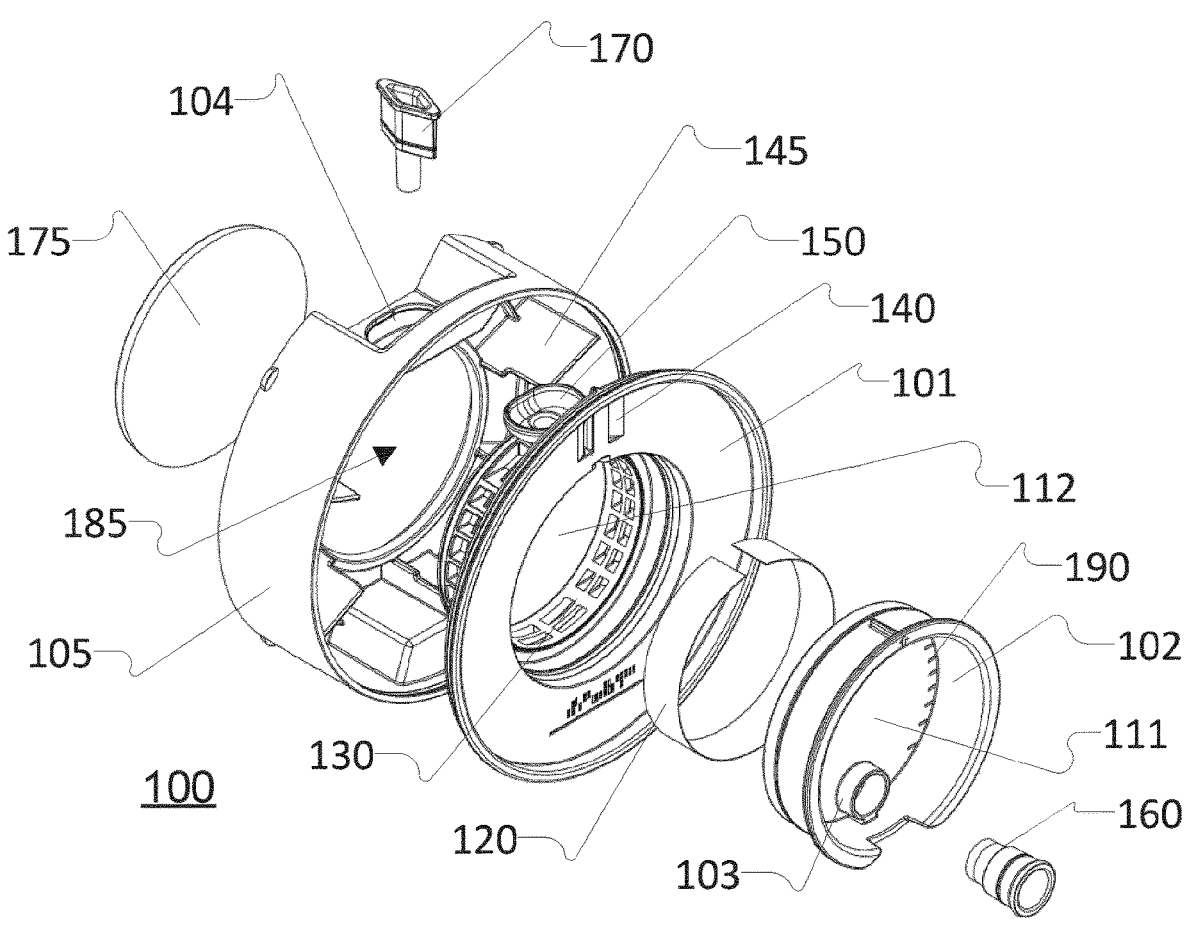

FIG. 7A correspond to FIG. 5B, FIG. 7B to FIG. 5C, FIG. 7C to FIG. 5D, FIG. 7D to FIG. 5E, and FIG. 7E to FIG. 6. A front view of the embodiment of FIGS. 7A-7E correspond to the front view of FIG. 5A.

FIG. 8 schematically illustrates a perspective view of a main housing 105 of a cell culture chamber device as disclosed herein.

Illustrated is a main housing 105 according to some embodiments and e.g. as shown in connection with the embodiments of FIGS. 5A-5E, 6, and 7A-7E more clearly showing certain features and aspects.

The main housing 105 comprises a cavity or open space and a first port 104 providing access to the enclosure (the port 104 to align in an assembled state of the cell culture chamber device with a further port; see e.g. 150 in FIG. 9B) where the port 104 is in fluidic connection with the enclosure 110.

The main housing 105 furthermore comprises a central opening 185 to be aligned with or receiving the second end (see e.g. 112 in FIGS. 5A-5E and elsewhere) in the assembled state of the cell culture chamber device. The main housing 105 is, as mentioned, configured to compactly receive a central housing (see e.g. 101 in FIGS. 9A and 9B).

In the particular shown embodiment, the main housing 105 furthermore comprises a number (here four as an example) of wall structure elements or similar 145 each for holding and/or supporting a water, liquid, or moisturizing element for embodiments also comprising a humidifier (please see further in the following). In alternative embodiments, the wall structure elements or similar 145 may be omitted. The wall structure elements or similar 145 may be distributed more or less evenly in the cavity or open space of the main housing 105 about a central axis/a rotational axis of the cell culture chamber device to distribute weigh of the water, liquid, or moisturizing elements more evenly. The wall structure elements or similar 145 may also provide structural integrity and/or support the received central housing.

In some embodiments and as shown, each (or some) wall structure element(s) or similar 145 comprises a cut-out or passage 141 forcing gas or air flow into close(r) proximity to a gas permeable membrane (see e.g. 120 in FIGS. 3, 5A, 6, and 7E).

Contained air or gas is in connection with a grid-like structure of the central housing (see e.g. 130 and 101 in FIGS. 9A and 9B and elsewhere) and finally the gas permeable membrane (see e.g. 120 in FIGS. 3, 5A, 6, and 7E). The grid-like structure provides support to the membrane while still allowing gas or air coming in contact with the membrane for gas exchange. The membrane may be secured, e.g. by welding, press-fitting, or gluing, to the grid-like structure. The gas permeable membrane is as mentioned configured to exchange gases, e.g. oxygen and carbon dioxide, with the content of the enclosure.

This readily provides a circumferential gas exchanger not blocking any line of sight between the first end and the second end in part defining the enclosure.

The function of the circumferential gas exchange system and the circumferential humidifier is further explained further in connection with FIG. 3.

FIGS. 9A and 9B schematically illustrate two perspective views of a central housing of a cell culture chamber device as disclosed herein.

Illustrated in FIGS. 9A and 9B is a first or central housing 101, in a transparent material, as disclosed herein more clearly illustrating the grid-like structure 130. Further illustrated are the second end 112, one or more fiducial and/or identification markers 155, one or more markings 115 in the form of a number of concentric circles 115 as an example, the gas exchange intake and outlet in the form of a double vent or similar 140, the further port 150, an aligning element 131.

FIG. 10 schematically illustrates a perspective view of a cover of a cell culture chamber device as disclosed herein.

Illustrated in FIG. 10 is a cover 102 in a transparent material. Further illustrated are the end 111, the closable and/or sealable port (first) port 103, and a number of level or fill-rate indicators 190.

Figure 11:
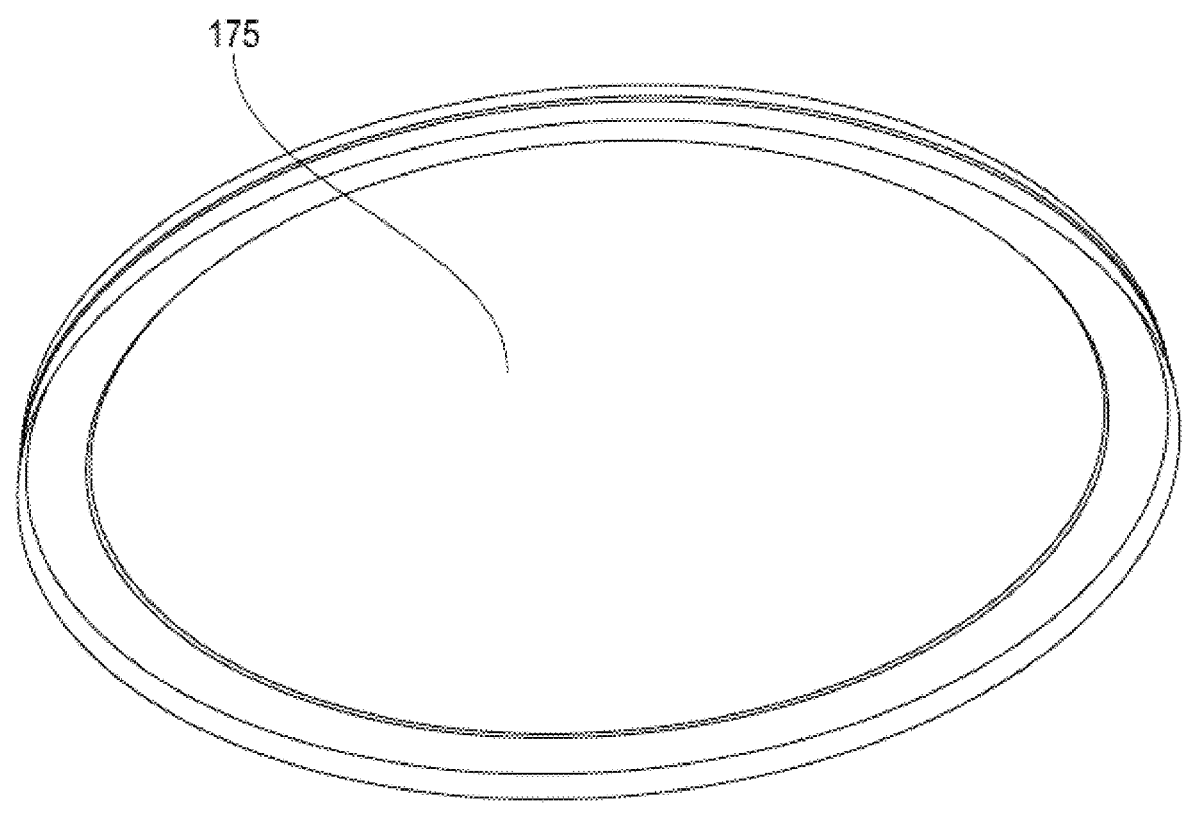
FIG. 11 schematically illustrates a perspective view of an optical diffusor as disclosed herein.

FIG. 11 schematically illustrates a perspective view of an optical diffusor as disclosed herein.

Illustrated is a circular optical diffusor 175. The optical diffusor 175 may be of any suitable translucent material where the refractive index is not uniform for the light of relevant wavelengths.

It is noted, that even though the shown optical diffusor 175 is substantially circular it could have other suitable shapes, e.g. square, rectangular, etc. The optical diffusor 175 may e.g. fit a window or part of a second end (see 112, 113 elsewhere), be curved to fit a connecting wall (see e.g. 114 elsewhere), etc.

In alternative embodiments, the diffusor 175 is not an optical diffusor but a diffusor 175 with respect to another type of illumination or visualisation signal, e.g. an acoustic diffusor or a diffusor for electromagnetic radiation different than light.

In some other alternative embodiments, the diffusor 175 (as disclosed herein) is replaced by a suitable reflector, e.g. a parabolic reflector, e.g. for use with front-lighting embodiments (or front-application of another type of illumination or visualisation signal) either in addition to or as an alternative to back-lighting or back-emission of another illumination or visualisation signal.

FIG. 12 schematically illustrates various embodiments with one or more light or illumination or visualisation signal sources arranged at different locations.

Illustrated is an enclosure as disclosed herein having a first end 111 and a second 112 connected by at least one connecting wall 114. Illustrated are three exemplary positions of where a light source 701 may be positioned depending on whether the second end 112 and/or the at least one connecting wall 114 is transparent or translucent. In some embodiments, several light sources 701 may be used. As mentioned, one or more light sources may e.g. located outside the second end 112 or the at least one connecting wall 114 or alternatively be integrated into such or also be arranged inside the enclosure. As a further alternative, one or more of the light sources 701 may be or comprises a fluorescent light emitting element.

In some alternative embodiments, the illustrated light source(s) 701 is/are replaced by one or more other illumination or visualisation signal sources 701, e.g. one or more acoustic transducers configured to emit acoustic waves, e.g. ultrasound, or one or more emitters configured to emit electromagnetic radiation other than light, e.g. infrared or x-rays.

Some preferred embodiments have been shown in the foregoing, but it should be stressed that the invention is not limited to these, but may be embodied in other ways within the subject matter defined in the following claims.

It should be emphasized that the term "comprises/comprising" when used in this specification is taken to specify the presence of stated features, elements, steps or components but does not preclude the presence or addition of one or more other features, elements, steps, components or groups thereof.

In the claims enumerating several features, some or all of these features may be embodied by one and the same element, component or item. The mere fact that certain measures are recited in mutually different dependent claims or described in different embodiments does not indicate that a combination of these measures cannot be used to advantage.

In the claims, any reference signs placed between parentheses shall not be constructed as limiting the claim. The word "comprising" does not exclude the presence of elements or steps other than those listed in a claim. The word "a" or "an" preceding an element does not exclude the presence of a plurality of such elements.

The mere fact that certain measures are recited in mutually different dependent claims does not indicate that a combination of these measures cannot be used to an advantage.

It will be apparent to a person skilled in the art that the various embodiments of the invention as disclosed and/or elements thereof can be combined without departing from the scope of the invention as defined in the claims.

The invention claimed is:

1. A cell culture chamber device for the growing of cell cultures and tissues, the cell culture chamber device comprising an enclosure configured to contain a cell culture media, and a first end, a second end, and at least one connecting wall connecting the first and the second ends, where the first end, the second end, and the at least one connecting wall at least in part defines the enclosure, wherein the cell culture chamber device is configured to rotate about a predetermined rotational axis, wherein the first end, or a part or window thereof, is substantially transparent and the second end and/or at least one of the at least one connecting wall, or a respective part or window thereof, is/are substantially transparent or is/are substantially translucent, where the first end or the part or window thereof is configured to be optically or otherwise aligned, at least for some period of time or periodically, with the second end or the part or window thereof and/or with the at least one of the at least one connecting wall or the part or window thereof so that light or another illumination or visualisation signal, transmitted through or by the second end or the part or window thereof and/or through or by the at least one of the at least one connecting wall or the part or window thereof into the enclosure, is transmitted or propagates through at least a part of the cell culture media and out through the first end or the part or window thereof to outside the cell culture chamber device while the cell culture chamber device is rotated about the predetermined rotational axis.

2. The cell culture chamber device according to claim 1, wherein the cell culture chamber device is configured for a use in or as part of a bioreactor, and/or wherein the first end or the part or window thereof and the second end or the part or window thereof are opposite each other in a predetermined direction, or along a central axis of the enclosure and/or the cell culture chamber device, where the central axis extends between the first end or the part or window thereof and the second end or the part or window thereof.

3. The cell culture chamber device according to claim 1, wherein the cell culture chamber device further comprises a circumferential gas exchanger arranged circumferentially about or along at least a part of the enclosure or about a predetermined rotational axis, and comprising a cavity comprising a volume connecting a gas exchange interface of the enclosure with ambient air or gas of the cell culture chamber device.

4. The cell culture chamber device according to claim 3, wherein the gas exchange interface is or comprises a circumferential gas permeable membrane configured to exchange gases with an inside and/or content of the enclosure where the circumferential gas permeable membrane is arranged circumferentially along a circumferential part of the enclosure and constitutes at least a part of at least one of the at least one connecting wall of the enclosure.

5. The cell culture chamber device according to claim 3, wherein the circumferential gas exchanger is connected with the ambient air or gas of the cell culture chamber device via at least one gas or air inlet and/or outlet, and wherein at least one of the at least one gas or air inlet and/or outlet is a double vent or port configured to draw in ambient air or gas into the cavity of the circumferential gas exchanger and expel air or gas out of the cavity of the circumferential gas exchanger in response to the cell culture chamber device being rotated thereby creating an air flow.

6. The cell culture chamber device according to claim 3, wherein the cell culture chamber device further comprises a circumferential humidifier arranged circumferentially about at least a part of the enclosure or about a predetermined rotational axis, and comprises or is connected to one or more liquid or moisturising reservoirs or elements configured to humidify or moisturise air or gas in at least a part of the cavity of the circumferential gas exchanger or of the air flow.

7. The cell culture chamber device according to claim 6, wherein a material or a group of materials of one or more predetermined parts of the enclosure and/or of the cell culture chamber device is or are opaque to UVC light, where the one or more predetermined parts are configured so no or substantially no UVC light can reach inside the enclosure, and/or wherein a material or a group of materials of the one or more liquid or moisturising reservoirs or elements and/or one or more predetermined parts of the cell culture chamber device is configured to allow transmission of UVC light to decontaminate a content of the one or more liquid or moisturising reservoirs or elements.

8. The cell culture chamber device according to claim 1, wherein the cell culture chamber device comprises a first or central housing and a cover where the first or central housing comprises the second end and the cover comprises the first end, and wherein the first or central housing is configured to receive the cover, where a cavity between the first or central housing and the cover is defined when the cover is received by the first or central housing, and where the resulting cavity defines at least a part of the enclosure.

9. The cell culture chamber device according to claim 8, wherein the cavity between the first or central housing and the cover comprises the circumferential gas permeable membrane constituting at least a part of the at least one the connecting wall of the enclosure thereby connecting the first end of the cover with the second end of the first or central housing, and/or a main housing configured to receive the first or central housing and the cover, or where the main housing comprises an opening aligning with the second end of the first or central housing when the first or central housing is received by or in the main housing, where the size of the opening is substantially of the same size as the second end.

10. The cell culture chamber device according to claim 9, wherein the main housing and the first or central housing, when received by the main housing defines the cavity of the circumferential gas exchanger, and wherein the first or central housing comprises the double vent or port arranged to be substantially perpendicular to the predetermined rotational axis.

11. The cell culture chamber device according to claim 1, wherein the second end or the part or window thereof is substantially transparent and wherein the cell culture chamber device further comprises or is connected to a light diffusor configured to receive light and to provide substantially uniform light to the second end or the part or window thereof thereby providing substantially uniform illumination of the cell culture media when contained in the enclosure, and/or wherein a respective cross section, substantially perpendicular to a central axis extending between the first and the second end, of the first end and/or the second end is/are substantially circular.

12. The cell culture chamber device according to claim 1, wherein the second end and/or at least one of the at least one connecting wall comprises one or more integrated light sources, and/or wherein the second end and/or at least one of the at least one connecting wall is/are or comprises a fluorescent light emitting element.

13. The cell culture chamber device according to claim 1, wherein the cell culture chamber device comprises a closable and/or sealable first port connected to an inside of the enclosure and a closable and/or sealable second port connected to the inside of the enclosure, where the first port and the second port are arranged on or to separate sides of the cell culture chamber device.

14. A cell culture chamber system for the growing of cell cultures and tissues, the cell culture chamber system comprising a cell culture chamber device according to claim 1.

15. The cell culture chamber system according to claim 14, wherein the cell culture chamber system comprises or is connected to an imaging, vision, or other registration or detection system or device and wherein at least one light source or another illumination or visualisation signal source is configured to emit light or the other illumination or visualisation signal received through the second end or the part or window thereof into the enclosure, and wherein the imaging, vision, or other registration or detection system or device is configured to capture at least a part of the light or the other illumination or visualisation signal transmitted through the first end or the part or window thereof to outside the enclosure.

16. The cell culture chamber device according to claim 1, wherein the first end or the part or window thereof and the second end or the part or window thereof are opposite each other in a predetermined direction along a lengthwise central axis of the enclosure and/or the cell culture chamber device where the central axis extends between the first end or the part or window thereof and the second end or the part or window thereof and the lengthwise central axis is the predetermined rotational axis.

17. The cell culture chamber device according to claim 1, wherein the cell culture chamber device and the enclosure is configured for clinostat rotation or for rotation negating or supplementing, at least to a certain extent, the effects of gravitational pull on content in the enclosure.

18. A cell culture chamber device for the growing of cell cultures and tissues, the cell culture chamber device comprising
an enclosure configured to contain a cell culture media,
a circumferential gas exchanger arranged circumferentially about or along at least a part of the enclosure or about a central and/or lengthwise axis of the cell culture chamber device, or about a predetermined rotational axis of the cell culture chamber device, wherein the circumferential gas exchanger comprises a cavity comprising a volume connecting a gas exchange interface of the enclosure with ambient air or gas of the cell culture chamber device.

19. A cell culture chamber device for the growing of cell cultures and tissues, the cell culture chamber device comprising an enclosure configured to contain a cell culture media, wherein a material or a group of materials of one or more predetermined parts of the enclosure and/or of the cell culture chamber device is or are opaque to UVC light and where the one or more predetermined parts are configured so no or substantially no UVC light can reach inside the enclosure and where another part thereof is substantially transparent to light, the cell culture chamber device having a lengthwise axis about which the cell culture chamber device is configured to rotate while light or another illumination or visualization signal transmitted through the part is transmitted or propagates through the cell culture chamber device to an outside thereof.

20. A cell culture chamber device for the growing of cell cultures and tissues, the cell culture chamber device comprising
an enclosure configured to contain a cell culture media, and
a first end, a second end, and at least one connecting wall connecting the first and the second ends, where the first end, the second end, and the at least one connecting wall at least in part defines the enclosure, wherein the first end, or a part or window thereof, is substantially transparent and the second end and/or at least one of the at least one connecting wall, or a respective part or window thereof, is/are substantially transparent or is/are substantially translucent, where the first end or the part or window thereof is configured to be optically or otherwise aligned, at least for some period of time or periodically, with the second end or the part or window thereof and/or with the at least one of the at least one connecting wall or the part or window thereof so that light or another illumination or visualisation signal, transmitted through or by the second end or the part or window thereof and/or through or by the at least one of the at least one connecting wall or the part or window thereof into the enclosure, is transmitted or propagates through at least a part of the cell culture media and out through the first end or the part or window thereof to outside the cell culture chamber device, and wherein the cell culture chamber device is configured to rotate about a predetermined rotational axis, and wherein the cell culture chamber device further comprises a circumferential gas exchanger arranged circumferentially about or along at least a part of the enclosure or about a central and/or lengthwise axis of the cell culture chamber device, or about a predetermined rotational axis, and comprising a cavity comprising a volume connecting a gas exchange interface of the enclosure with ambient air or gas of the cell culture chamber device.

21. A cell culture chamber device for the growing of cell cultures and tissues, the cell culture chamber device comprising an enclosure configured to contain a cell culture media, and a first end, a second end, and at least one connecting wall connecting the first and the second ends, where the first end, the second end, and the at least one connecting wall at least in part defines the enclosure, wherein the first end, or a part or window thereof, is substantially transparent and the second end and/or at least one of the at least one connecting wall, or a respective part or window thereof, is/are substantially transparent or is/are substantially translucent, where the first end or the part or window thereof is configured to be optically or otherwise aligned, at least for some period of time or periodically, with the second end or the part or window thereof and/or with the at least one of the at least one connecting wall or the part or window thereof so that light or another illumination or visualisation signal, transmitted through or by the second end or the part or window thereof and/or through or by the at least one of the at least one connecting wall or the part or window thereof into the enclosure, is transmitted or propagates through at least a part of the cell culture media and out through the first end or the part or window thereof to outside the cell culture chamber device, and wherein the cell culture chamber device is configured to rotate about a predetermined rotational axis, wherein the second end or the part or window thereof is substantially transparent and wherein the cell culture chamber device further comprises or is connected to a light diffusor configured to receive light and to provide substantially uniform light to the second end or the part or window thereof thereby providing substantially uniform illumination of the cell culture media when contained in the enclosure, and/or wherein a respective cross section, substantially perpendicular to a central axis extending between the first and the second end, of the first end and/or the second end is/are substantially circular.

22. A cell culture chamber device for the growing of cell cultures and tissues, the cell culture chamber device comprising an enclosure configured to contain a cell culture media, and a first end, a second end, and at least one connecting wall connecting the first and the second ends, where the first end, the second end, and the at least one connecting wall at least in part defines the enclosure, wherein the first end, or a part or window thereof, is substantially transparent and the second end and/or at least one of the at least one connecting wall, or a respective part or window thereof, is/are substantially transparent or is/are substantially translucent, where the first end or the part or window thereof is configured to be optically or otherwise aligned, at least for some period of time or periodically, with the second end or the part or window thereof and/or with the at least one of the at least one connecting wall or the part or window thereof so that light or another illumination or visualisation signal, transmitted through or by the second end or the part or window thereof and/or through or by the at least one of the at least one connecting wall or the part or window thereof into the enclosure, is transmitted or propagates through at least a part of the cell culture media and out through the first end or the part or window thereof to outside the cell culture chamber device, and wherein the cell culture chamber device is configured to rotate about a predetermined rotational axis, wherein the first end or the part or window thereof and the second end or the part or window thereof are opposite each other in a predetermined direction along a lengthwise central axis of the enclosure and/or the cell culture chamber device where the central axis extends between the first end or the part or window thereof and the second end or the part or window thereof and the lengthwise central axis is the predetermined rotational axis.

23. A cell culture chamber device for the growing of cell cultures and tissues, the cell culture chamber device comprising an enclosure configured to contain a cell culture media, and a first end, a second end, and at least one connecting wall connecting the first and the second ends, where the first end, the second end, and the at least one connecting wall at least in part defines the enclosure, wherein the first end, or a part or window thereof, is substantially transparent and the second end and/or at least one of the at least one connecting wall, or a respective part or window thereof, is/are substantially transparent or is/are substantially translucent, where the first end or the part or window thereof is configured to be optically or otherwise aligned, at least for some period of time or periodically, with the second end or the part or window thereof and/or with the at least one of the at least one connecting wall or the part or window thereof so that light or another illumination or visualisation signal, transmitted through or by the second end or the part or window thereof and/or through or by the at least one of the at least one connecting wall or the part or window thereof into the enclosure, is transmitted or propagates through at least a part of the cell culture media and out through the first end or the part or window thereof to outside the cell culture chamber device, and wherein the cell culture chamber device is configured to rotate about a predetermined rotational axis, wherein the cell culture chamber device and the enclosure are configured for clinostat rotation or for rotation negating or supplementing, at least to a certain extent, the effects of gravitational pull on content in the enclosure.

\* \* \* \* \*